(12) United States Patent
Kayama et al.

(10) Patent No.: US 10,564,120 B2
(45) Date of Patent: Feb. 18, 2020

(54) GAS CONCENTRATION DETECTION DEVICE

(71) Applicant: DENSO CORPORATION, Kariya, Aichi-pref. (JP)

(72) Inventors: Ryozo Kayama, Kariya (JP); Yukihiro Yamashita, Kariya (JP)

(73) Assignee: DENSO CORPORATION, Kariya (JP)

( * ) Notice: Subject to any disclaimer, the term of this patent is extended or adjusted under 35 U.S.C. 154(b) by 108 days.

(21) Appl. No.: 15/328,732

(22) PCT Filed: Jul. 24, 2015

(86) PCT No.: PCT/JP2015/003716
§ 371 (c)(1),
(2) Date: Jan. 24, 2017

(87) PCT Pub. No.: WO2016/013229
PCT Pub. Date: Jan. 28, 2016

(65) Prior Publication Data
US 2017/0219513 A1 Aug. 3, 2017

(30) Foreign Application Priority Data

Jul. 25, 2014 (JP) .................................. 2014-151790
Jul. 10, 2015 (JP) .................................. 2015-138342

(51) Int. Cl.
*G01N 27/406* (2006.01)
*G01N 27/407* (2006.01)
(Continued)

(52) U.S. Cl.
CPC ..... *G01N 27/4065* (2013.01); *G01N 27/4073* (2013.01); *G01N 27/41* (2013.01);
(Continued)

(58) Field of Classification Search
CPC .............. G01N 27/4065; G01N 27/41; G01N 27/4073; G01N 27/26; G01N 27/416; G01N 27/407; G01N 27/409
See application file for complete search history.

(56) References Cited

U.S. PATENT DOCUMENTS 6,551,497 B1\* 4/2003 Gao .................... G01N 27/4065
204/425
9,494,549 B2\* 11/2016 Yoshida ............... G01N 27/409
(Continued)

FOREIGN PATENT DOCUMENTS

JP 2001-141696 5/2001
JP 2003-120399 4/2003
(Continued)

*Primary Examiner* — Gurpreet Kaur
*Assistant Examiner* — Vivian A Tran
(74) *Attorney, Agent, or Firm* — Nixon & Vanderhye P.C.

(57) ABSTRACT

A gas concentration detection device includes a pump cell, a sensor cell, a monitor cell, a sensor current detection unit detecting a current outputted by the sensor cell, a monitor current detection unit detecting a current outputted by the monitor cell, a voltage adjustment unit adjusting a pump cell voltage applied to the pump cell, and a sensitivity determination unit determining a gas sensitivity of at least one of the sensor cell or the monitor cell. The voltage adjustment unit changes the pump cell voltage from a target voltage into a detection voltage where the concentration of the residual oxygen supplied to the sensor cell and the monitor cell is increased. The sensitivity determination unit determines the gas sensitivity based on a detection current detected by at least one of the sensor current detection unit or the monitor current detection unit in accordance with the concentration of the residual oxygen.

18 Claims, 12 Drawing Sheets

(51) Int. Cl.
*G01N 27/41* (2006.01)
*G01N 27/409* (2006.01)
*G01N 27/26* (2006.01)
*G01N 27/416* (2006.01)

(52) U.S. Cl.
CPC ........... *G01N 27/26* (2013.01); *G01N 27/407* (2013.01); *G01N 27/409* (2013.01); *G01N 27/416* (2013.01)

(56) References Cited

U.S. PATENT DOCUMENTS

| | | | |
|---|---|---|---|
| 2003/0121310 A1* | 7/2003 | Tomura | G01N 27/419 73/31.05 |
| 2004/0221641 A1 | 11/2004 | Moritsugu et al. | |
| 2007/0119708 A1* | 5/2007 | Oya | G01N 27/4175 204/401 |
| 2011/0083423 A1* | 4/2011 | Kadowaki | F02D 41/0002 60/276 |
| 2011/0233060 A1* | 9/2011 | Horisaka | G01N 27/409 204/412 |
| 2014/0238853 A1* | 8/2014 | Yoshida | G01N 27/409 204/401 |
| 2015/0128572 A1* | 5/2015 | Fujiwara | F01N 3/20 60/284 |

FOREIGN PATENT DOCUMENTS

| | | | |
|---|---|---|---|
| JP | 2004271515 A * | 9/2004 | ......... G01N 27/4175 |
| JP | 2007-147386 | 6/2007 | |
| JP | 2007147386 A † | 6/2007 | |
| JP | 4042545 | 11/2007 | |
| JP | 2009-175013 | 8/2009 | |
| JP | 2009175013 A * | 8/2009 | |
| JP | 2015-59926 | 3/2015 | |
| JP | 2015-64341 | 4/2015 | |
| WO | WO 2016/121380 | 4/2016 | |

\* cited by examiner
† cited by third party

GAS CONCENTRATION DETECTION DEVICE

CROSS REFERENCE TO RELATED APPLICATION

This application is the U.S. national phase of International Application No. PCT/JP2015/003716 filed on Jul. 24, 2015 which designated the U.S. and claims priority to Japanese Patent Application No. 2014-151790 filed on Jul. 25, 2014 and Japanese Patent Application No. 2015-138342 filed on Jul. 10, 2015, the entire contents of each of which are incorporated herein by reference.

TECHNICAL FIELD

The present disclosure relates to a gas concentration detection device that detects a specific gas component concentration in exhaust gas of an internal combustion engine.

BACKGROUND ART

A nitrogen oxide (NOx) sensor is known as a sensor that detects the concentration of NOx as one of the specific gas components contained in the exhaust gas discharged from an internal combustion engine. The NOx sensor is placed on, for example, the downstream side of a selective reduction-type NOx catalyst in a diesel engine exhaust gas purification system using the NOx catalyst. The NOx concentration that is detected by the NOx sensor placed as described above is used for the control of a reducing agent addition amount added to the NOx catalyst.

Also known is a NOx sensor that has a first pump electrode in a first chamber and a second pump electrode and a pump electrode for NOx detection in a second chamber (refer to, for example, Patent Literature 1). According to Patent Literature 1, the first pump electrode causes a decomposition reaction by means of inter-electrode voltage application and discharges oxygen out of the first chamber. The second pump electrode discharges oxygen out of the second chamber by means of inter-electrode voltage application. The pump electrode for NOx detection reacts to NOx gas in gas by means of inter-electrode voltage application and outputs a NOx concentration in the form of a current signal.

Each cell that constitutes the NOx sensor deteriorates as a poisoning substance is deposited on its cell surface as a result of a catalytic reaction and this deterioration results in a decline in the detection accuracy or detection sensitivity of the NOx sensor. Examples of the poisoning substance include those derived from manganese and silicon, which are additives contained in fuel oil.

According to the NOx sensor deterioration determination method that is disclosed in Patent Literature 1 below, the NOx concentration in exhaust gas reaching a NOx sensor is forcibly fluctuated and an abnormality is determined in a case where the fluctuation of an output value outputted by the NOx sensor at that time deviates from a normal fluctuation.

PRIOR ART LITERATURES

Patent Literature

Patent Literature 1: JP2003-120399A

SUMMARY OF INVENTION

According to the deterioration determination method that is disclosed in Patent Literature 1, the range of the fluctuation of the NOx concentration that is forced to fluctuate needs to be widened for a good grasp of the fluctuation of the output value from the NOx sensor. Accordingly, exhaust emission deterioration is inevitable during deterioration determination.

The present disclosure has been made in view of such circumstances, and an object thereof is to provide a gas concentration detection device that is capable of determining a decline in gas sensitivity and requires no significant fluctuation of the concentration of a specific gas component as gas to be measured.

According to an aspect of the present disclosure, the gas concentration detection device includes a pump cell (246) discharging an oxygen out of a measurement chamber (242) from an exhaust gas of an internal combustion engine (20) introduced into the measurement chamber, a sensor cell (248) detecting a residual oxygen concentration in the exhaust gas from which the oxygen is discharged and a specific gas concentration in the exhaust gas, a monitor cell (249) detecting a concentration of a residual oxygen in the exhaust gas from which the oxygen is discharged, a sensor current detection unit (101) detecting a current outputted by the sensor cell, a monitor current detection unit (102) detecting a current outputted by the monitor cell, a voltage adjustment unit (104) adjusting a pump cell voltage applied to the pump cell, and a sensitivity determination unit (106) determining a gas sensitivity of at least one of the sensor cell or the monitor cell. The voltage adjustment unit changes the pump cell voltage from a target voltage into a detection voltage where the concentration of the residual oxygen supplied to the sensor cell and the monitor cell is increased. The sensitivity determination unit determines the gas sensitivity based on a detection current detected by at least one of the sensor current detection unit or the monitor current detection unit in accordance with the concentration of the residual oxygen which is increased.

According to the present disclosure, the pump cell voltage is lowered from the target voltage and becomes the detection voltage, and thus the oxygen corresponding to the detection voltage flows from the pump cell side to the monitor cell and sensor cell sides. The residual oxygen concentration in the case of voltage application to the pump cell at the detection voltage exceeds the residual oxygen concentration in the case of voltage application to the pump cell at the target voltage. Because the currents outputted by the monitor cell and the sensor cell are currents corresponding to the residual oxygen concentration, the detection current of the deteriorated cell is lowered as a result of the deterioration when one of the monitor cell and the sensor cell deteriorates and its gas sensitivity is reduced, and thus the deterioration of that cell can be grasped. In this manner, the gas sensitivity can be determined without the concentration of the gas in the exhaust gas to be measured having to be fluctuated to a significant extent.

According to the present disclosure, the gas concentration detection device that is capable of determining a decline in gas sensitivity and requires no significant fluctuation of the concentration of a gas to be measured can be provided.

BRIEF DESCRIPTION OF DRAWINGS

The above and other objects, features and advantages of the present disclosure will become more apparent from the following detailed description made with reference to the accompanying drawings. In the drawings.

DESCRIPTION OF EMBODIMENTS

Figure 1:
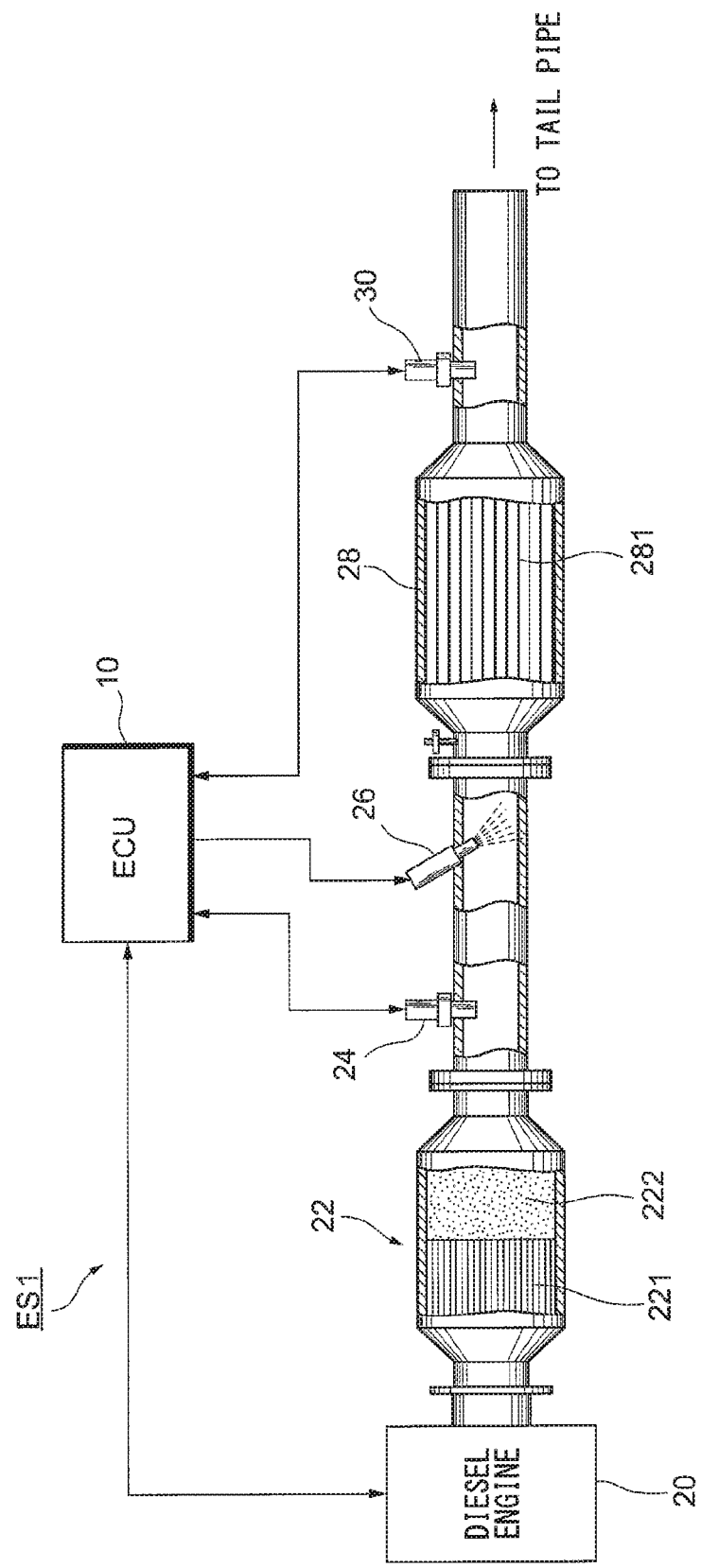
FIG. 1 is a diagram schematically illustrating an engine exhaust system in which an ECU according to a first embodiment of the present disclosure is used.

Embodiments of the present disclosure will be described hereafter referring to drawings. In the embodiments, a part that corresponds to a matter described in a preceding embodiment may be assigned with the same reference numeral, and redundant explanation for the part may be omitted.

First Embodiment

As illustrated in FIG. 1, an ECU 10 is a device that controls a diesel engine 20 and an engine exhaust system ES1 connected thereto. The ECU 10 functions to control a behavior of the diesel engine 20. The ECU 10 adjusts a fuel injection valve opening degree based on an accelerator opening degree and an engine rotation speed.

In the engine exhaust system ES1, a diesel oxidation catalyst converter 22 and a selective catalytic reduction (SCR) catalytic converter 28 are disposed in this order from the diesel engine 20 side. The diesel oxidation catalyst converter 22 has a diesel oxidation catalyst (DOC) 221 and a diesel particulate filter (DPF) 222.

The diesel oxidation catalyst converter 22, which removes a harmful substance from exhaust gas by oxidation or reduction, is a device that collects particulate matter (PM) which has carbon and the like in particular.

A ceramic carrier, an oxide mixture having aluminum oxide, cerium dioxide, and zirconium dioxide as its components, and a precious metal catalyst such as platinum, palladium, and rhodium are main constituents of the diesel oxidation catalyst 221. The diesel oxidation catalyst 221 removes hydrocarbon, carbon monoxide, nitrogen oxide, and the like from the exhaust gas by oxidation. In addition, the diesel oxidation catalyst 221 raises an exhaust gas temperature by using heat that is generated during a catalytic reaction.

The diesel particulate filter 222 has the form of a honeycomb structure in which a platinum group catalyst such as platinum and palladium is carried by porous ceramic. The diesel particulate filter 222 causes the particulate matter contained in the exhaust gas to be deposited on a partition wall of the honeycomb structure. The deposited particulate matter is removed through combustion-based oxidation. An increase in temperature in the diesel oxidation catalyst 221 and a decline in combustion temperature of the particulate matter caused by an additive are used for this combustion.

The SCR catalytic converter 28 is a device that reduces NOx into nitrogen and water as a post-processing device of the diesel oxidation catalyst converter 22 and has an SCR 281 that is a selective reduction-type catalyst. Examples of the SCR 281 can include a catalyst in which a precious metal such as Pt is carried on a surface of a base material such as zeolite and alumina. The SCR 281 reduces and removes NOx when a catalyst temperature is within an active temperature range and urea as a reducing agent is added. A urea addition injector 26 for urea addition is disposed on an upstream side of the SCR catalytic converter 28.

In the present embodiment, a NOx sensor 24 is placed between the diesel oxidation catalyst converter 22 and the urea addition injector 26 and a NOx sensor 30 is placed on a downstream side of the SCR catalytic converter 28.

The amount of the urea that is added from the urea addition injector 26 to the SCR catalytic converter 28 is determined based on a NOx concentration detected by the NOx sensor 24 and a NOx concentration detected by the NOx sensor 30. More specifically, the NOx sensor 24 determines the amount of the urea that is added based on the NOx concentration detected from the exhaust gas before passage through the SCR catalytic converter 28. In addition, the NOx sensor 30 corrects the amount of the urea that is added by performing feedback such that the NOx concentration detected from the exhaust gas after the passage through the SCR catalytic converter 28 becomes as low in value as possible. The NOx in the exhaust gas is properly reduced in the SCR 281 by the urea being added from the urea addition injector 26 to the SCR 281 in accordance with the amount of the addition determined in this manner described above. In this manner, the hydrocarbon, carbon monoxide, and nitrogen oxide contained in the exhaust gas are discharged to the outside from a tail pipe (not illustrated) after passing through the NOx sensor 24 and the NOx sensor 30.

The ECU 10 functions as a control unit responsible for controlling of the diesel engine 20 and equipment around the diesel engine 20. The ECU 10 includes a CPU, a RAM, a ROM, input/output ports, and a storage device. The following description of the present embodiment will focus on a function of the ECU 10 as a deterioration determination device that determines deteriorations of the NOx sensors 24 and 30. Because the NOx sensor 24 and the NOx sensor 30 have the same configuration, the following description will cover the configuration of the NOx sensor 24 as an example along with a configuration of the ECU 10. In the present embodiment, a gas concentration detection device has the NOx sensor 24 and the ECU 10.

Figure 2:
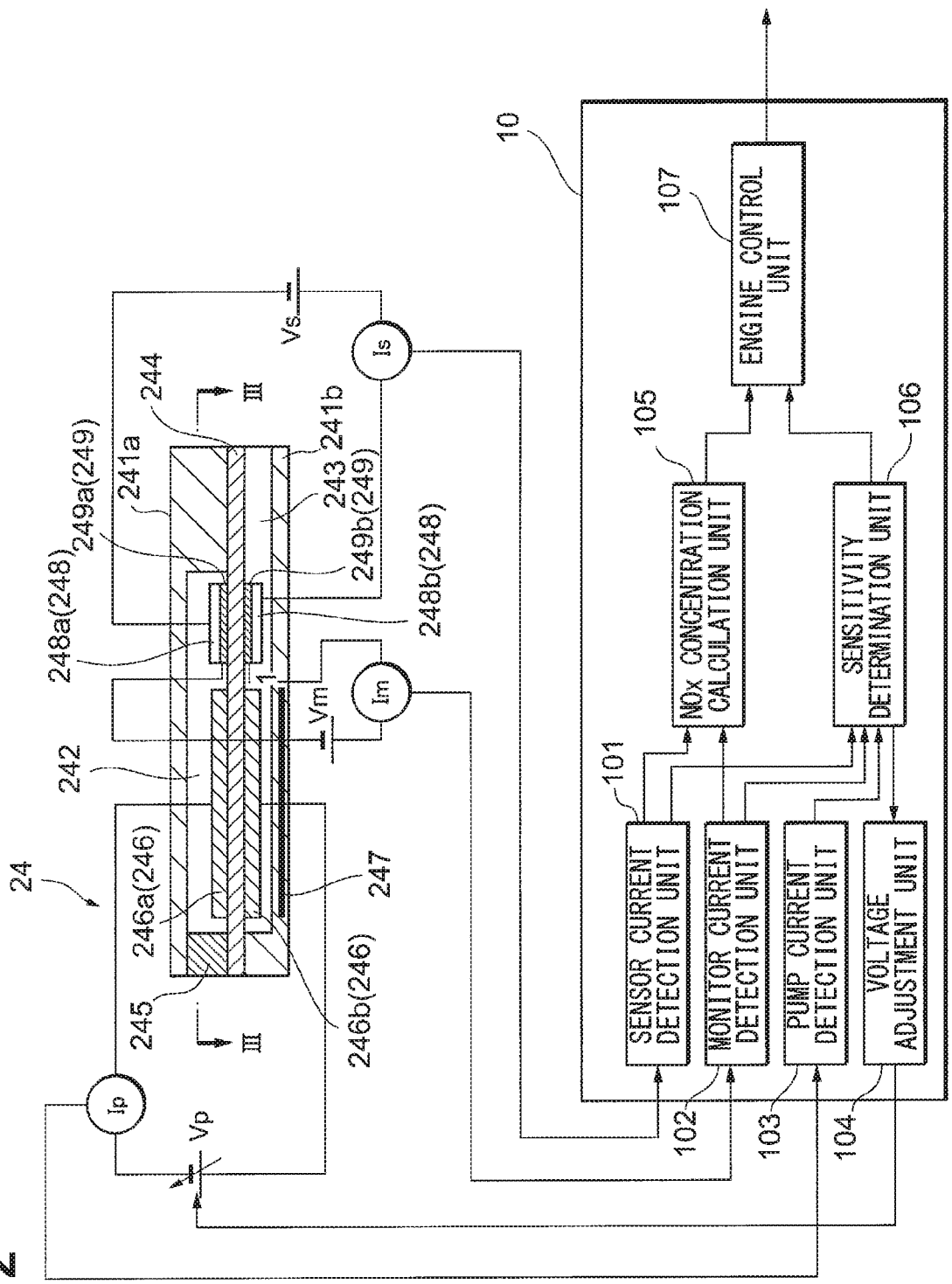
FIG. 2 is a diagram schematically illustrating a configuration of a NOx sensor that is illustrated in FIG. 1 and a control-related configuration of the ECU.
Figure 3:
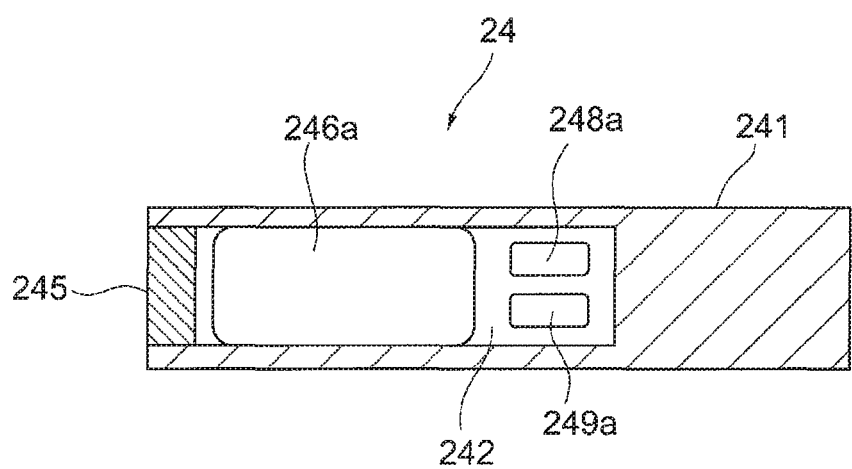
FIG. 3 is a cross-sectional view illustrating an III-III cross section in FIG. 2.

As illustrated in FIGS. 2 and 3, the NOx sensor 24 is provided with a first main body portion 241a, a second main body portion 241b, a solid electrolyte body 244, a diffusion resistive element 245, pump electrodes 246a and 246b, a heater 247, sensor electrodes 248a and 248b, and monitor electrodes 249a and 249b.

The solid electrolyte body 244 is a plate-shaped member and an oxygen ion-conducting solid electrolyte material such as zirconia oxide constitutes the solid electrolyte body 244. The first main body portion 241a and the second main body portion 241b are placed with the solid electrolyte body 244 placed therebetween. A recessed portion that is disposed to retreat from the solid electrolyte body 244 side is formed in the first main body portion 241a and the concave portion functions as a measurement chamber 242. One side surface of the measurement chamber 242 is open and the diffusion resistive element 245 is placed in the open side surface. The diffusion resistive element 245 is formed from a porous material or a material in which a pore is formed. A velocity of the exhaust gas that is drawn into the measurement chamber 242 is controlled by an action of the diffusion resistive element 245.

A recessed portion that is disposed to retreat from the solid electrolyte body 244 side is formed in the second main body portion 241b as well and the concave portion functions as an atmospheric chamber 243. One side surface of the atmospheric chamber 243 is open. Gas drawn into the atmospheric chamber 243 from the solid electrolyte body 244 side is released to the atmosphere.

The cathode side pump electrode 246a is disposed on the diffusion resistive element 245 side and a surface of the solid electrolyte body 244 facing the measurement chamber 242 side. The anode side pump electrode 246b is disposed at a position corresponding to the pump electrode 246a on a surface of the solid electrolyte body 244 facing the atmospheric chamber 243. The pump electrode 246a, the pump electrode 246b, and the solid electrolyte body 244 interposed between the pump electrode 246a and the pump electrode 246b constituting a pump cell 246.

Once a voltage Vp is applied between the pump electrodes 246a and 246b, the oxygen that is contained in the exhaust gas in the measurement chamber 242 comes into contact with the cathode side pump electrode 246a and becomes an oxygen ion. The oxygen ion flows through the solid electrolyte body 244 toward the anode side pump electrode 246b, becomes oxygen with its charge released in the pump electrode 246b, and is discharged into the atmosphere from the atmospheric chamber 243.

The higher the voltage that is applied to the pump electrodes 246a and 246b, the greater the amount of the oxygen that is discharged from the exhaust gas by the pump cell 246. The lower the voltage that is applied to the pump electrodes 246a and 246b, the smaller the amount of the oxygen that is discharged from the exhaust gas by the pump cell 246. Accordingly, the amount of the residual oxygen that is contained in the exhaust gas which flows through a monitor cell 249 and a sensor cell 248 in a subsequent stage can be increased and decreased by the voltage applied to the pump electrodes 246a and 246b being increased and decreased.

The cathode side monitor electrode 249a is disposed on the side opposite to the diffusion resistive element 245 across the pump electrode 246a (downstream side than the pump electrode 246a) and the surface of the solid electrolyte body 244 facing the measurement chamber 242 side. The anode side monitor electrode 249b is disposed at a position corresponding to the monitor electrode 249a on the surface of the solid electrolyte body 244 facing the atmospheric chamber 243. The monitor electrode 249a, the monitor electrode 249b, and the solid electrolyte body 244 interposed between the monitor electrode 249a and the monitor electrode 249b constituting the monitor cell 249.

The monitor cell 249 detects a concentration of the oxygen remaining in the exhaust gas from which the oxygen has been discharged by the pump cell 246. Once a voltage Vm is applied to the monitor electrodes 249a and 249b, the residual oxygen that is contained in the exhaust gas from which the oxygen has been discharged by the pump cell 246 comes into contact with the cathode side monitor electrode 249a and becomes an oxygen ion. The oxygen ion flows through the solid electrolyte body 244 toward the anode side monitor electrode 249b, becomes oxygen with its charge released in the monitor electrode 249b, and is discharged into the atmosphere from the atmospheric chamber 243. The charge at this time is detected as a current Im by a monitor current detection unit 102 and the residual oxygen concentration in the exhaust gas can be calculated based on the current Im.

The cathode side sensor electrode 248a is disposed on the side opposite to the diffusion resistive element 245 across the pump electrode 246a and the surface of the solid electrolyte body 244 facing the measurement chamber 242 side. The anode side sensor electrode 248b is disposed at a position corresponding to the sensor electrode 248a on the surface of the solid electrolyte body 244 facing the atmospheric chamber 243. The sensor electrode 248a, the sensor electrode 248b, and the solid electrolyte body 244 interposed between the sensor electrode 248a and the sensor electrode 248b constituting the sensor cell 248.

The sensor electrode 248a has a platinum-rhodium alloy (Pt—Rh alloy) and has a high level of reducibility with respect to NOx. NOx brought into contact with the sensor electrode 248a is subjected to reductive decomposition into $N_2$ and $O_2$. Once a voltage Vs is applied to the sensor electrodes 248a and 248b, $O_2$ resulting from the decomposition receives a charge from the cathode side sensor electrode 248a and becomes an oxygen ion. The oxygen ion flows through the solid electrolyte body 244 toward the anode side sensor electrode 248b, becomes oxygen with its charge released in the sensor electrode 248b, and is discharged into the atmosphere from the atmospheric chamber 243. The charge at this time is detected as a current Is by a sensor current detection unit 101 and the concentration of the NOx and the residual oxygen concentration in the exhaust gas can be calculated based on the current Is.

The ECU 10 is configured as a digital processor provided with a memory with an analog circuit constituting a part of the ECU 10 or the ECU 10 as a whole. In any of both cases, functional control blocks are configured in the ECU 10 for a function to output a control signal based on a received electrical signal to be achieved. FIG. 2 is a control block diagram illustrating the functional control blocks of the ECU 10. A software module that is incorporated into the analog circuit or the digital processor constituting the ECU 10 does not necessarily have to be divided into the control blocks illustrated in FIG. 2, may be configured as one carrying out working of multiple control blocks, and may be further subdivided. An actual internal configuration of the ECU 10 can be appropriately changed by those skilled in the art insofar as the configuration allows a processing flow to be executed by the ECU 10.

Functional components of the ECU 10 will be described below. The ECU 10 is provided with the sensor current detection unit 101, the monitor current detection unit 102, a pump current detection unit 103, a voltage adjustment unit 104, a NOx concentration calculation unit 105, a sensitivity determination unit 106, and an engine control unit 107.

The sensor current detection unit 101 is a part that detects the current Is outputted by the sensor cell 248. The sensor current detection unit 101 outputs a signal indicating the detected current Is to the NOx concentration calculation unit 105 and the sensitivity determination unit 106.

The monitor current detection unit 102 is a part that detects the current Im outputted by the monitor cell 249. The monitor current detection unit 102 outputs a signal indicating the detected current Im to the NOx concentration calculation unit 105 and the sensitivity determination unit 106.

The pump current detection unit 103 is a part that detects a current Ip outputted by the pump cell 246. The pump current detection unit outputs a signal indicating the detected current Ip to the sensitivity determination unit 106.

The voltage adjustment unit 104 is a part that adjusts a voltage applied to the pump cell 246. During a normal operation when no deterioration determination is made, the voltage adjustment unit 104 applies a target voltage depending on an operation situation of the diesel engine 20 to the pump cell 246. During the deterioration determination, the voltage adjustment unit 104 applies a detection voltage, which is lower than the target voltage, to the pump cell 246.

The NOx concentration calculation unit 105 is a part that calculates the NOx concentration in the exhaust gas based on the current Is detected by the sensor current detection unit 101 and the current Im detected by the monitor current detection unit 102. The NOx concentration calculation unit 105 calculates the NOx concentration in the exhaust gas excluding a current value attributable to the residual oxygen concentration in the exhaust gas detected by the sensor cell 248 by subtracting the output current Im outputted by the monitor cell 249 from the current Is outputted by the sensor cell 248. The NOx concentration calculation unit 105 outputs a signal indicating the calculated NOx concentration to the engine control unit 107.

The sensitivity determination unit 106 is a part that determines gas sensitivity of at least one of the sensor cell 248 or the monitor cell 249 based on at least one of the current Is detected by the sensor current detection unit 101 or the current Im detected by the monitor current detection unit 102. According to the present disclosure, at least one of the sensor cell 248 or the monitor cell 249 is equivalent to the sensor cell 248, the monitor cell 249, or both the sensor cell 248 and the monitor cell 249. The gas sensitivity refers to a ratio of a detected amount to an actual amount of the NOx and oxygen reaching the sensor cell 248 and the monitor cell 249. Accordingly, assuming that the gas sensitivity in a case where the sensor cell 248 and the monitor cell 249 are not deteriorated at all is "1", the gas sensitivity is "0.8" when the actual amount of the NOx and oxygen is 10 and the detected amount is 8. The gas sensitivity falls as the sensor cell 248 and the monitor cell 249 deteriorate, and thus it can be said that the sensitivity determination unit 106 determines the deteriorations of the sensor cell 248 and the monitor cell 249. The sensitivity determination unit 106 outputs a signal indicating the determined gas sensitivity to the engine control unit 107.

The engine control unit 107 is a part that controls the diesel engine 20 and the urea addition injector 26 based on signals output from the NOx sensors 24 and 30 and other sensors and a program stored in advance. The engine control unit 107 performs correction with respect to the control of the diesel engine 20 based on the signal outputted by the sensitivity determination unit 106 and indicating the gas sensitivity and performs an operation for displaying the gas sensitivity on a monitor or the like.

Figure 4:
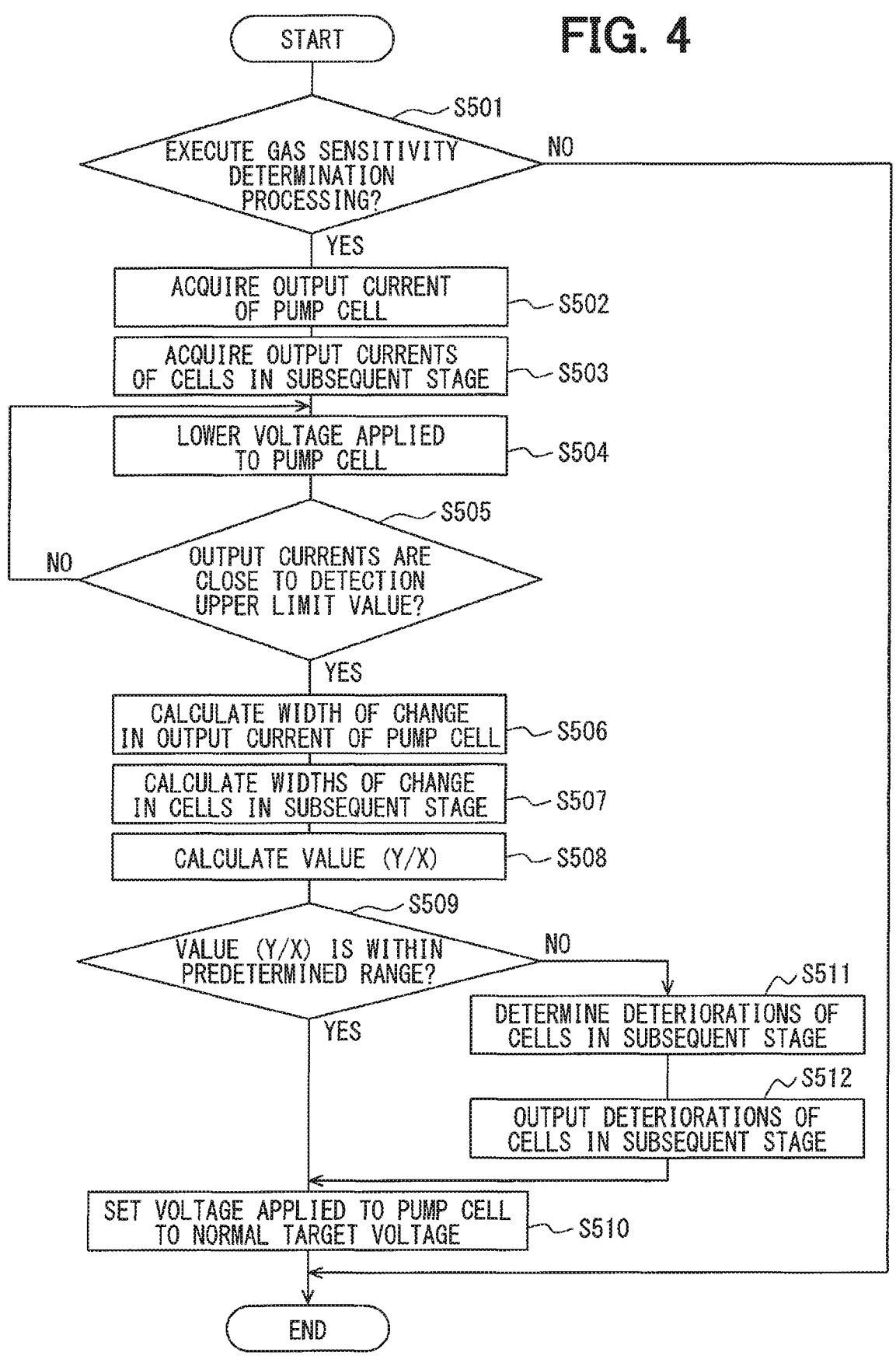
FIG. 4 is a flowchart illustrating as sensitivity determination processing regarding the NOx sensor that is illustrated in FIGS. 1 to 3.

Hereinafter, gas sensitivity determination processing regarding the NOx sensor 24 that is conducted by the ECU 10 will be described with reference to FIG. 4. The sensitivity determination unit 106 determines whether or not to execute the gas sensitivity determination processing (Step S501). The sensitivity determination unit 106 determines that the gas sensitivity determination processing is to be performed in a state where the exhaust gas that is taken in by the NOx sensor 24 has a stable state and exhaust gas components are predictable and determines that the gas sensitivity determination processing is not to be performed in a state where the exhaust gas that is taken in by the NOx sensor 24 does not have the stable state and the exhaust gas components are unpredictable.

Examples of the state where the exhaust gas has the stable state and the exhaust gas components are predictable can include a case where the diesel engine 20 is in a fuel cut situation. Because no fuel is injected in the diesel engine 20, air that is taken into the diesel engine 20 is taken in by the NOx sensor 24 as it is (although the air might contain a very small amount of impurities). When most of the exhaust gas components taken in by the NOx sensor 24 are air as described above, the voltage Vp applied to the pump cell 246 and a theoretical value of a current corresponding thereto are determined. The current Ip that is outputted by the pump cell 246 can be actually measured, and thus a deterioration situation regarding the pump cell 246 can be grasped based on a divergence with respect to the theoretical value. The amount of the oxygen flowing through the sensor cell 248 and the monitor cell 249 in a case where the voltage Vp is applied to the pump cell 246 can be grasped in view of the deterioration situation. Accordingly, once the currents Is and Im flowing through the sensor cell 248 and the monitor cell 249 are detected, the gas sensitivity and a deterioration degree of the sensor cell 248 and the monitor cell 249 can be grasped based on whether or not a current corresponding to the amount of the oxygen that has flowed in is flowing. The sensitivity determination unit 106 allows the processing to proceed to Step S502 in the case of the determination to perform the gas sensitivity determination processing and terminates the processing in the case of the determination not to perform the gas sensitivity determination processing.

In a case where the sensitivity determination unit 106 makes the determination that the gas sensitivity determination processing is to be executed, the sensitivity determination unit 106 acquires the signal indicating the output current Ip of the pump cell 246 detected by the pump current detection unit 103 (Step S502). The output of the signal indicating the current Ip from the pump current detection unit 103 to the sensitivity determination unit 106 continues until processing in Step S506, and thus the current Ip can be continuously monitored by the sensitivity determination unit 106.

Subsequently, the sensitivity determination unit 106 acquires the signal indicating the output current Is of the sensor cell 248 detected by the sensor current detection unit 101. In addition, the sensitivity determination unit 106 acquires the signal indicating the output current Im of the monitor cell 249 detected by the monitor current detection unit 102. The sensitivity determination unit 106 acquires the output currents Im and Is of the sensor cell 248 and the monitor cell 249, which are cells in the subsequent stage (Step S503). The output of the signals indicating the current Is and the current Im from the sensor current detection unit 101 and the monitor current detection unit 102 to the sensitivity determination unit 106 continues until processing in Step S507, and thus the current Is and the current Im can be continuously monitored by the sensitivity determination unit 106.

Subsequently, the sensitivity determination unit 106 outputs an instruction signal for lowering the voltage Vp applied to the pump cell 246 to the voltage adjustment unit 104. The voltage adjustment unit 104 lowers the voltage Vp applied to the pump cell 246 (Step S504). It is preferable that the voltage Vp applied to the pump cell 246 is lowered in stages by a predetermined width at a time and it is also preferable that the voltage Vp applied to the pump cell 246 is steplessly lowered at a constant rate or at a predetermined change rate.

Figure 5:
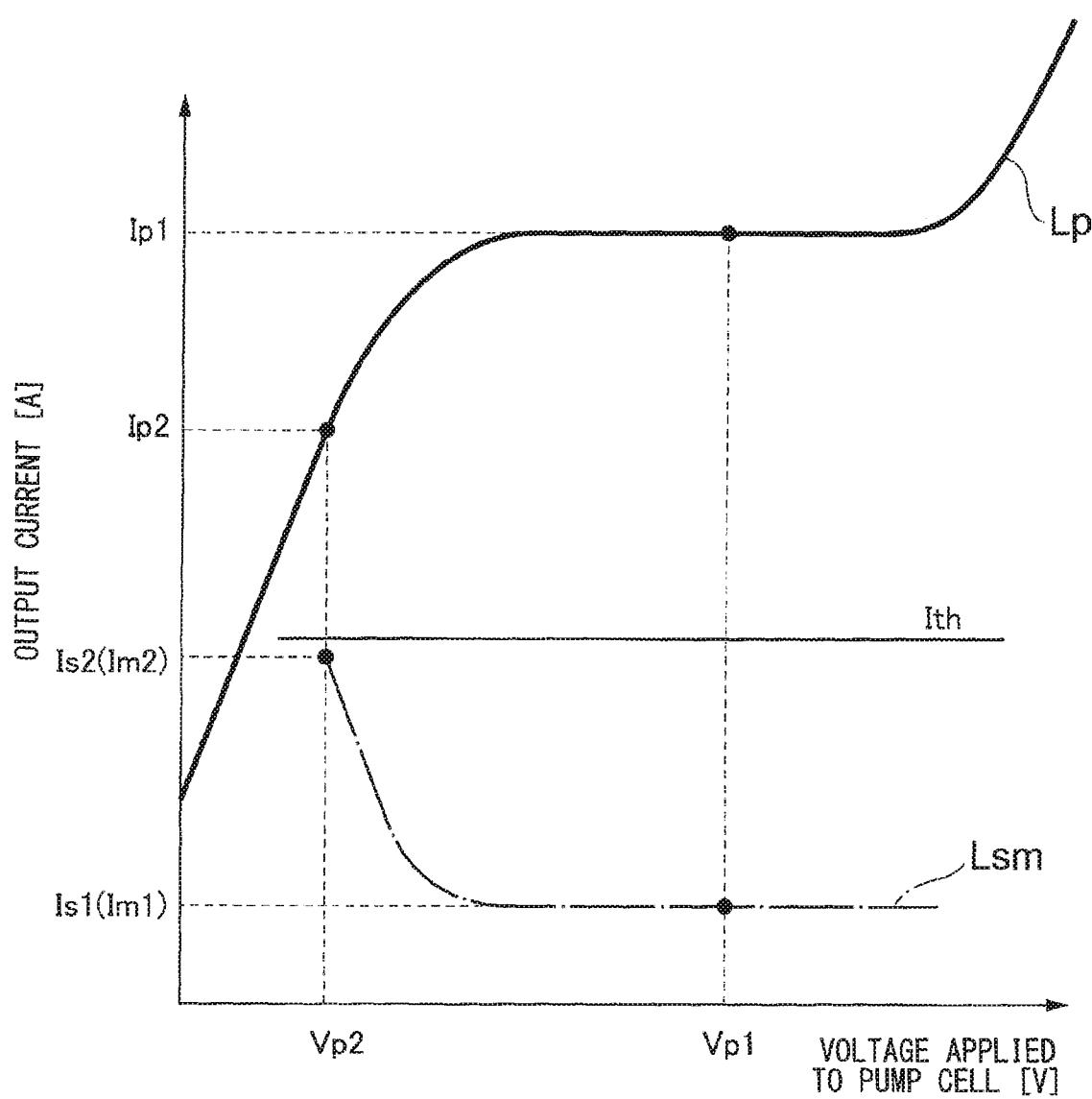
FIG. 5 is a graph illustrating the gas sensitivity determination processing that is illustrated in FIG. 4.

A relationship among the voltage Vp applied to the pump cell 246, the output current Ip outputted by the pump cell 246, the current Is outputted by the sensor cell, and the current Im outputted by the monitor cell is illustrated in FIG. 5. In FIG. 5, a horizontal axis represents the voltage Vp applied to the pump cell 246 and a vertical axis represents the output current outputted by each of the cells.

The target voltage of the pump cell 246 during the normal operation is Vp1. The target voltage Vp1 is a value that is specified based on the operation situation of the diesel engine 20 and is set such that the amount of the exhaust gas drawn into the measurement chamber 242 is an appropriate amount. As illustrated by a line Lp in FIG. 5, the output current Ip of the pump cell 246 is constant for a while as the voltage Vp applied to the pump cell 246 is lowered from the normal target voltage Vp1, and then the output current Ip of the pump cell 246 gently falls before its slope is stabilized with the change in the voltage Vp and the current Ip having a proportional relationship.

Once the voltage Vp applied to the pump cell 246 is lowered, the amount of the oxygen reaching the cells in the subsequent stage including the sensor cell 248 and the monitor cell 249 increases, and then the output current Is and the output current Im increase soon. As illustrated by a line Lsm in FIG. 5, the output current Is and the output current Im are constant for a while and then are gently increased as the voltage Vp applied to the pump cell 246 is lowered, and then the slope of the increase becomes constant after some time. The slope is stable up to a vicinity of a detection upper limit value Ith of the output currents Im and Is (maximum value of a measurable current), In a region where the slope is stable as described above, an output current value with respect to the amount of the oxygen reaching the sensor cell 248 and the monitor cell 249 is stable, and thus the region is suitable for determining the gas sensitivity of the sensor cell 248 and the monitor cell 249.

The sensitivity determination unit 106 determines whether or not the output current Is of the sensor cell 248 and the output current Im of the monitor cell are close to the detection upper limit value Ith (Step S505). The sensitivity determination unit 106 sets the voltage Vp applied to the pump cell 246 as a voltage Vp2 for detection such that the detection values of the output currents Im and Is become close to the detection upper limit value Ith. The sensitivity determination unit 106 sets the voltage Vp2 for detection and allows the processing to proceed to Step S506 when the output current Is and the output current Im are close to the detection upper limit value Ith and continues to execute the processing in Step S504 when the output current Is and the output current Im are not close to the detection upper limit value Ith.

In the present embodiment, the values of the output current Is of the sensor cell 248 and the output current Im of the monitor cell are monitored as described above and the voltage applied to the pump cell 246 is adjusted based on whether or not the region suitable for determining the gas sensitivity of the sensor cell 248 and the monitor cell 249 is reached. In a case where the NOx sensor 24 according to the present embodiment is used, the sensor cell 248 and the monitor cell 249, which are the cells in the subsequent stage, have a current detection range of nano-ampere order whereas the pump cell 246 has a current detection range of milliampere order. In some cases, the magnitude difference between the current detection ranges may lead to a significant change in the output currents of the sensor cell 248 and the monitor cell 249 resulting from a slight change in the voltage applied to the pump cell 246. In this regard, the voltage applied to the pump cell 246 is adjusted while the output currents of the sensor cell 248 and the monitor cell 249 are directly monitored, which allows the voltage applied to the pump cell 246 to be set with a higher level of accuracy.

Also preferable from this point of view is fixing for a certain period of time in a state where a single width of reduction is set during the lowering in stages and by the predetermined width at a time from the normal target voltage Vp1 in Step S504. A noise element can be removed and accurate output current detection can be performed when fixing for a predetermined period of time is performed at a predetermined voltage, changes in the output currents Ip, Im, and Is at that time are detected, and an average value of each is taken. The voltage Vp2 for detection is not limited to the use of the single voltage value and may allow multiple setting in the form of, for example, a first detection voltage and a second detection voltage that is lower than the first detection voltage. In other words, the accuracy of the output current detection can be enhanced when multiple points where the slopes of the output currents Ip, Im, and Is appear with accuracy are measured and the multiple points are set as the voltages for detection.

Subsequently, the sensitivity determination unit 106 calculates a width of change X in the output current Ip of the pump cell 246 (Step S506). The sensitivity determination unit 106 calculates output current Ip1-output current Ip2 as the width of change X.

The sensitivity determination unit 106 calculates widths of change Y in the output current Is of the sensor cell 248 and the output current Im of the monitor cell 249 (Step S507). The sensitivity determination unit 106 calculates output current Is1-output current Is2 as the width of change Y and output current Im1-output current Im2 as the width of change Y.

The sensitivity determination unit 106 calculates a value (Y/X), which is obtained by the width of change Y being divided by the width of change X (Step S508). The sensitivity determination unit 106 determines whether or not the value (Y/X) obtained by the width of change Y being divided by the width of change X is within a predetermined range (Step S509). Y/X being within the predetermined range implies that a reaction in accordance with the residual oxygen amount excluding the amount of the oxygen removed in the pump cell 246 is being performed by the sensor cell 248 and the monitor cell 249 and implies that the deteriorations of the sensor cell 248 and the monitor cell 249 are within an allowable range. Y/X being out of the predetermined range implies that the reaction in accordance with the residual oxygen amount excluding the amount of the oxygen removed in the pump cell 246 is not being performed by the sensor cell 248 and the monitor cell 249 and implies that the deteriorations of the sensor cell 248 and the monitor cell 249 are out of the allowable range.

When Y/X is within the predetermined range, it can be determined that the sensitivity of the sensor cell 248 and the monitor cell 249 is normal and the deteriorations of the sensor cell 248 and the monitor cell 249 are within the allowable range. The voltage adjustment unit 104 sets the voltage applied to the pump cell 246 to the normal target voltage Vp1 and terminates the gas sensitivity determination processing regarding the NOx sensor 24 (Step S510).

When Y/X is out of the predetermined range, it is determined that the sensitivity of the sensor cell 248 and the monitor cell 249 is abnormal and the deteriorations of the sensor cell 248 and the monitor cell 249 deviate from the allowable range (Step S511). In a case where the deteriorations of the sensor cell 248 and the monitor cell 249 deviate from the allowable range, it is preferable that determination content is changed based on whether the degree of the deterioration (degree of the deviation from the allowable range) is high or low.

A response is made by means of current value correction in a case where the degree of the deterioration is low and the correction of the values of the currents output from the sensor cell 248 and the monitor cell 249 is regarded as resulting in accurate current values despite the deviation of the deteriorations of the sensor cell 248 and the monitor cell 249 from the allowable range. The sensitivity determination unit 106 outputs, to the engine control unit 107, information showing the current values output from the sensor cell 248 and the monitor cell 249 and information showing the degrees of the deteriorations and correction factors (Step S512). The engine control unit 107 controls the diesel engine 20 and controls injection by the urea addition injector 26 based on the information output from the sensitivity determination unit 106.

In a case where the deteriorations of the sensor cell 248 and the monitor cell 249 deviate from the allowable range and the degree of the deterioration is high, a numerical value regarded as an accurate current value cannot be obtained despite the correction of the values of the currents output from the sensor cell 248 and the monitor cell 249. The sensitivity determination unit 106 outputs, to the engine control unit 107, information showing the current values output from the sensor cell 248 and the monitor cell 249, the degrees of the deteriorations, and information for urging exchange (Step S512). The engine control unit 107 controls the diesel engine 20 and the injection by the urea addition injector 26 based on the information output from the sensitivity determination unit 106 and performs notification by means of a notification unit such as a predetermined lamp being lighted and a buzzer performing sound-generating vibration.

The sensitivity determination unit 106 outputs an instruction signal to the voltage adjustment unit 104 such that the voltage applied to the pump cell 246 is set to the normal target voltage Vp1. The voltage adjustment unit 104 returns the voltage applied to the pump cell 246 to the normal target voltage Vp1 and terminates the gas sensitivity determination processing regarding the NOx sensor 24 (Step S510).

In the first embodiment described above, the sensitivity determination unit 106 calculates output current Is1-output current Is2 as the width of change Y, calculates output current Im1-output current Im2 as the width of change Y, and calculates the output ratio (Y/X) by dividing the width of change Y by the width of change X. When Y/X is within the predetermined range, the sensitivity determination unit 106 determines that the sensitivity of the sensor cell 248 and the monitor cell 249 is normal and the deteriorations of the sensor cell 248 and the monitor cell 249 are within the allowable range. The gas sensitivity determination processing regarding the sensor cell 248 and the monitor cell 249 is not limited thereto and can be executed by various methods.

When the output ratio Y/X is used, a voltage Vps lower than the normal target voltage Vp1 can also be used as an applied voltage at a point in time when an increase in the output currents Is and Im is assumed and the voltage Vp2 for detection can also be used as an applied voltage lower than the voltage Vps. This setting of the voltages Vps and Vp2 allows the sensitivity determination to be performed with a higher level of stability.

Figure 6:
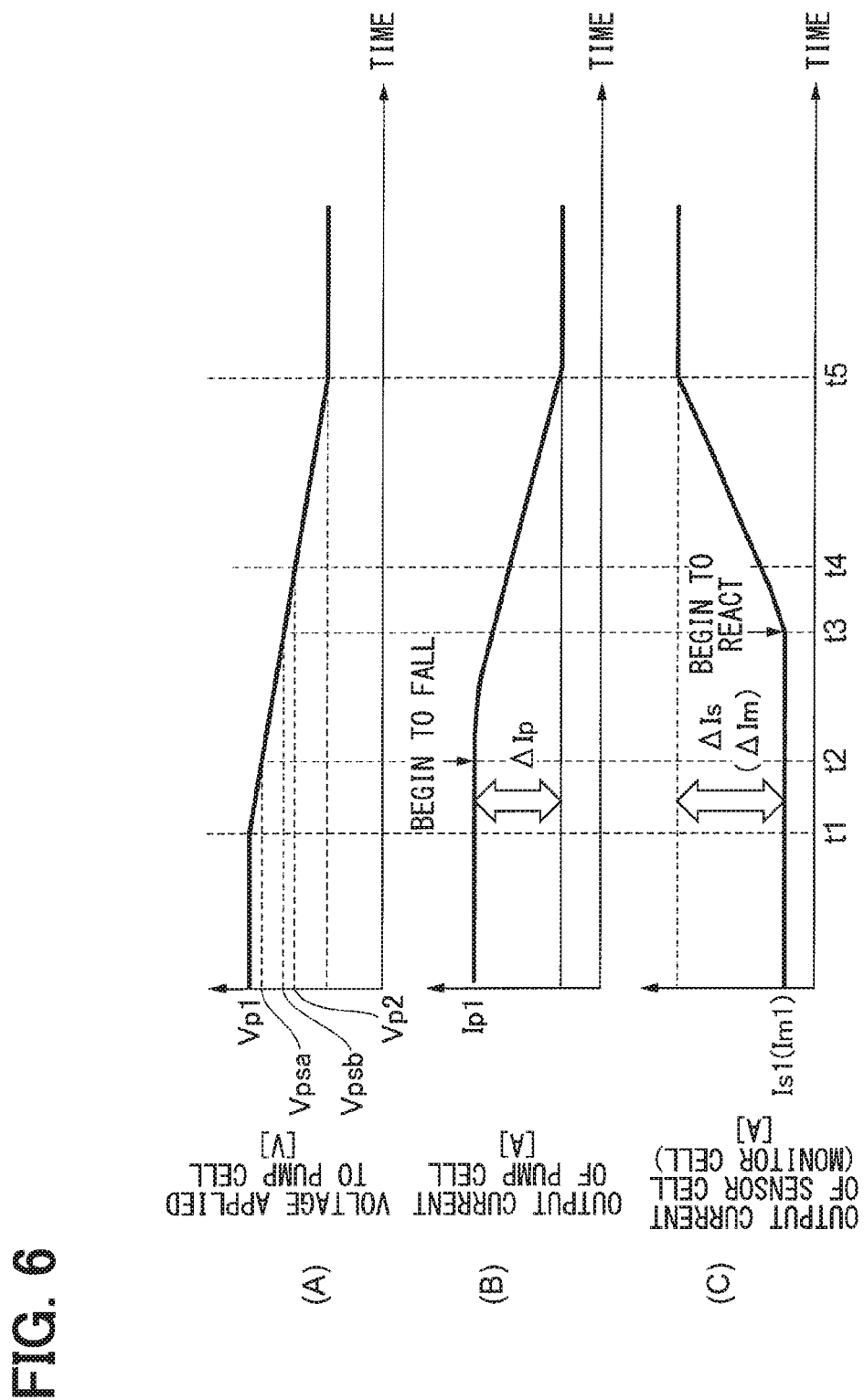
FIG. 6 is a graph illustrating the gas sensitivity determination processing that is illustrated in FIG. 4.

A method for setting the voltages Vps and Vp2 in a case where the output ratio Y/X is used will be described with reference to FIG. 6. FIG. 6 is time charts illustrating the current outputted by the pump cell 246 and the currents outputted by the sensor cell 248 and the monitor cell 249 with respect to the voltage applied to the pump cell 246, (A) of FIG. 6 shows the voltage applied to the pump cell 246 with time. (B) of FIG. 6 shows the current outputted by the pump cell 246 with time. (C) of FIG. 6 shows the currents outputted by the sensor cell 248 and the monitor cell 249 with time.

The voltage applied to the pump cell 246 begins to gradually fall at time t1 after being maintained at the normal target voltage Vp1. A decline in the output current of the pump cell 246 occurs with a delay from the decline in the applied voltage, and thus the output current of the pump cell 246 begins to fall at time t2 subsequent to time t1. The output current of the pump cell 246 gradually falls until time t5 after beginning to fall at time t2.

Once the output current of the pump cell 246 begins to decrease at time t2, the amount of the oxygen supplied to the sensor cell 248 and the monitor cell 249 increases in response to the decline in the output current. When the output current of the pump cell 246 has a narrow width of decline, the amount of increase in the amount of the oxygen supplied to the sensor cell 248 and the monitor cell 249 is small, and thus the output currents of the sensor cell 248 and the monitor cell 249 are not increased insofar as the width of the decline in the output current of the pump cell 246 does not exceed a predetermined amount. This is because a negative pressure is unlikely to be generated in a vicinity of the sensor cell 248 and the monitor cell 249 and the oxygen equivalent to the amount of decline in the output current of the pump cell 246 is not supplied to the sensor cell 248 and monitor cell 249 side when the amount of the oxygen reacting in the sensor cell 248 and the monitor cell 249 is small. Accordingly, the output currents of the sensor cell 248 and the monitor cell 249 begin to be increased at time t3 subsequent to time t2.

The voltage Vps can be used as a voltage Vpsa at which the output current of the pump cell 246 begins to fall and the voltage Vp2 for detection can be used as a voltage at time t4, which is subsequent to a timing at which the sensor cell 248 and the monitor cell 249 begin to react. In comparison to the case of the use of the normal target voltage Vp1, the use of the voltage Vpsa allows the output ratio Y/X to be obtained at a timing closer to the timing at which the sensor cell 248 and the monitor cell 249 begin to react.

The voltage Vps can be used as a voltage Vpsb at which the output currents of the sensor cell 248 and the monitor cell 249 begin to be increased and the voltage Vp2 for detection can be used as the voltage at time t4, which is subsequent to the timing at which the sensor cell 248 and the monitor cell 249 begin to react. In comparison to the case of the use of the voltage Vps as the voltage Vpsa at which the output current of the pump cell 246 begins to fall, the use of the voltage Vpsb allows the output ratio Y/X to be obtained at a timing closer to the timing at which the sensor cell 248 and the monitor cell 249 begin to react.

Because the output currents of the sensor cell 248 and the monitor cell 249 are weak currents, the detection accuracy is high and the detection accuracy increases when the output currents are increased. Since the output currents of the sensor cell 248 and the monitor cell 249 are the weak currents, the current detection determination during the determination of the output ratio Y/X becomes rate-limiting of the output currents of the sensor cell 248 and the monitor cell 249. As described above, the output currents of the sensor cell 248 and the monitor cell 249 are increased after a decline in the output current of the pump cell 246 and an increase in the amount of the oxygen supply to the sensor cell 248 and the monitor cell 249 because of the structure of the NOx sensor 24. In view of all these considerations, it can be said that the use of the voltage Vps as the voltage Vpsb at which the output currents of the sensor cell 248 and the monitor cell 249 begin to be increased constitutes a more preferable method.

Figure 7:
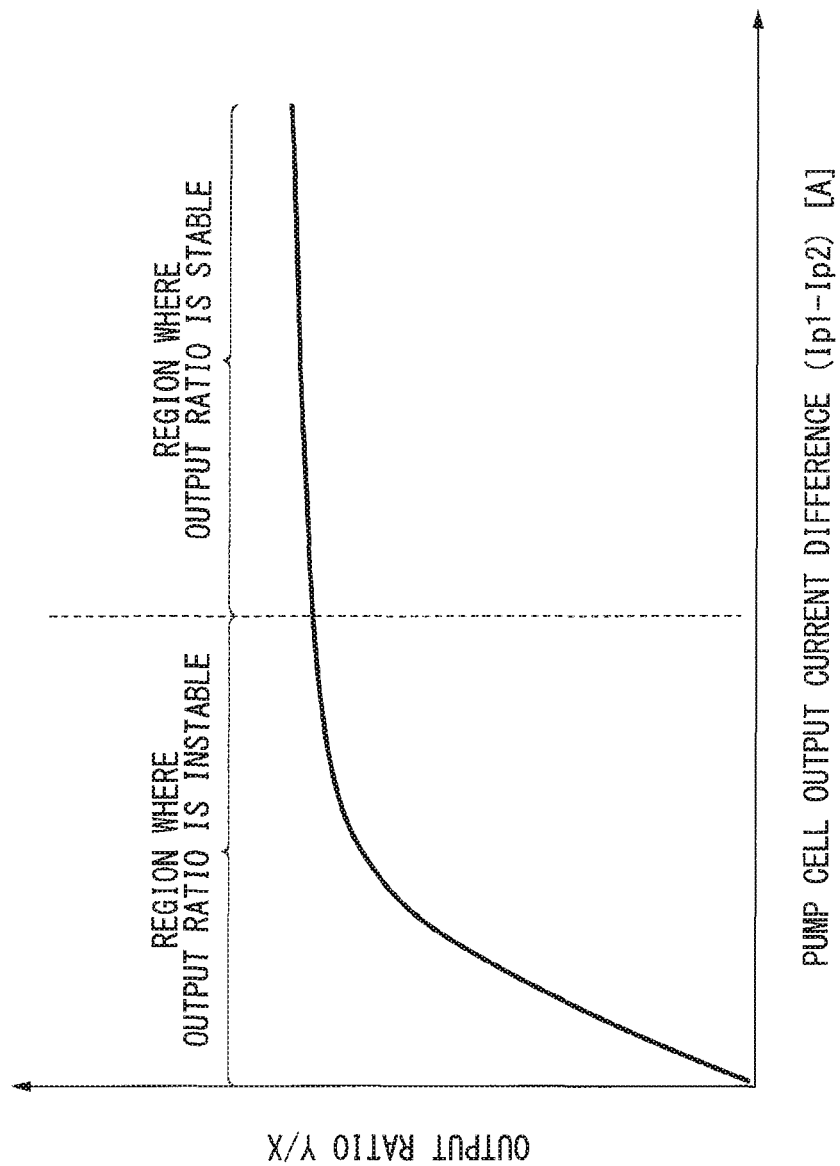
FIG. 7 is a graph illustrating the gas sensitivity determination processing that is illustrated in FIG. 4.

A relationship between the pump cell output current difference (Ip1-Ip2) and the output ratio Y/X is illustrated in FIG. 7. As illustrated in FIG. 7, the output ratio Y/X is put into a region of instability when the pump cell output current difference (Ip1-Ip2) is excessively reduced. As described above, the output currents of the sensor cell 248 and the monitor cell 249 are increased after the output current of the pump cell 246 is reduced. Accordingly, the output ratio Y/X cannot be accurately calculated and the output ratio Y/X is in the region of instability until an increase in the output currents of the sensor cell 248 and the monitor cell 249. From this viewpoint, it is preferable that the voltage Vp2 for detection applied to the pump cell 246 is determined within a range of incomplete reduction. Accordingly, it is desirable that the voltage Vp2 for detection applied to the pump cell 246 is determined within a region where a large pump cell output current difference (Ip1-Ip2) can be set (region where the output ratio is stable), that is, a range lower than a predetermined value as illustrated in FIG. 7.

A determination based on a current absolute value in a case where the voltage applied to the pump cell 246 is lowered is another method for the sensitivity determination unit 106 determining the deteriorations of the sensor cell 248 and the monitor cell 249. The determination is made based on an output current Is2 of the sensor cell 248 and an output current Im2 of the monitor cell 249 in a case where the voltage applied to the pump cell 246 is lowered and the output current of the pump cell 246 is lowered. When the output currents Is2 and Im2 are within a predetermined range, it can be determined that the sensitivity of the sensor cell 248 and the monitor cell 249 is normal and the deteriorations of the sensor cell 248 and the monitor cell 249 are within the allowable range.

The determination can also be made based on a differential output current ΔIs of the sensor cell 248 (=Is2−Is1) and a differential output current ΔIm of the monitor cell 249 (=Im2−Im1) in the case of the lowering of the voltage applied to the pump cell 246. When the differential output currents ΔIs and ΔIm are within a predetermined range, it can be determined that the sensitivity of the sensor cell 248 and the monitor cell 249 is normal and the deteriorations of the sensor cell 248 and the monitor cell 249 are within the allowable range. During exhaust gas measurement, a voltage is applied to the pump cell 246, the sensor cell 248, and the monitor cell 249. Because of the voltage application, the current flows through the pump cell 246, the sensor cell 248, and the monitor cell 249 even in the event of no exhaust gas inflow and the current varies with temperature. Accordingly, it is preferable that the determination is made based on the differential output currents ΔIs and ΔIm for an effect attributable to a temperature difference to be ruled out.

A determination based on a response speed in the case of the lowering of the voltage applied to the pump cell 246 is another method for the sensitivity determination unit 106 determining the deteriorations of the sensor cell 248 and the monitor cell 249. The determination is made based on the output current Is2 of the sensor cell 248 and the output current 1m2 of the monitor cell 249 after the elapse of a predetermined period of time in the case of the lowering of the voltage applied to the pump cell 246 and the lowering of the output current of the pump cell 246. When the output currents Is2 and Im2 are within a predetermined range after the elapse of the predetermined period of time, it can be determined that the sensitivity of the sensor cell 248 and the monitor cell 249 is normal and the deteriorations of the sensor cell 248 and the monitor cell 249 are within the allowable range.

Figure 8:
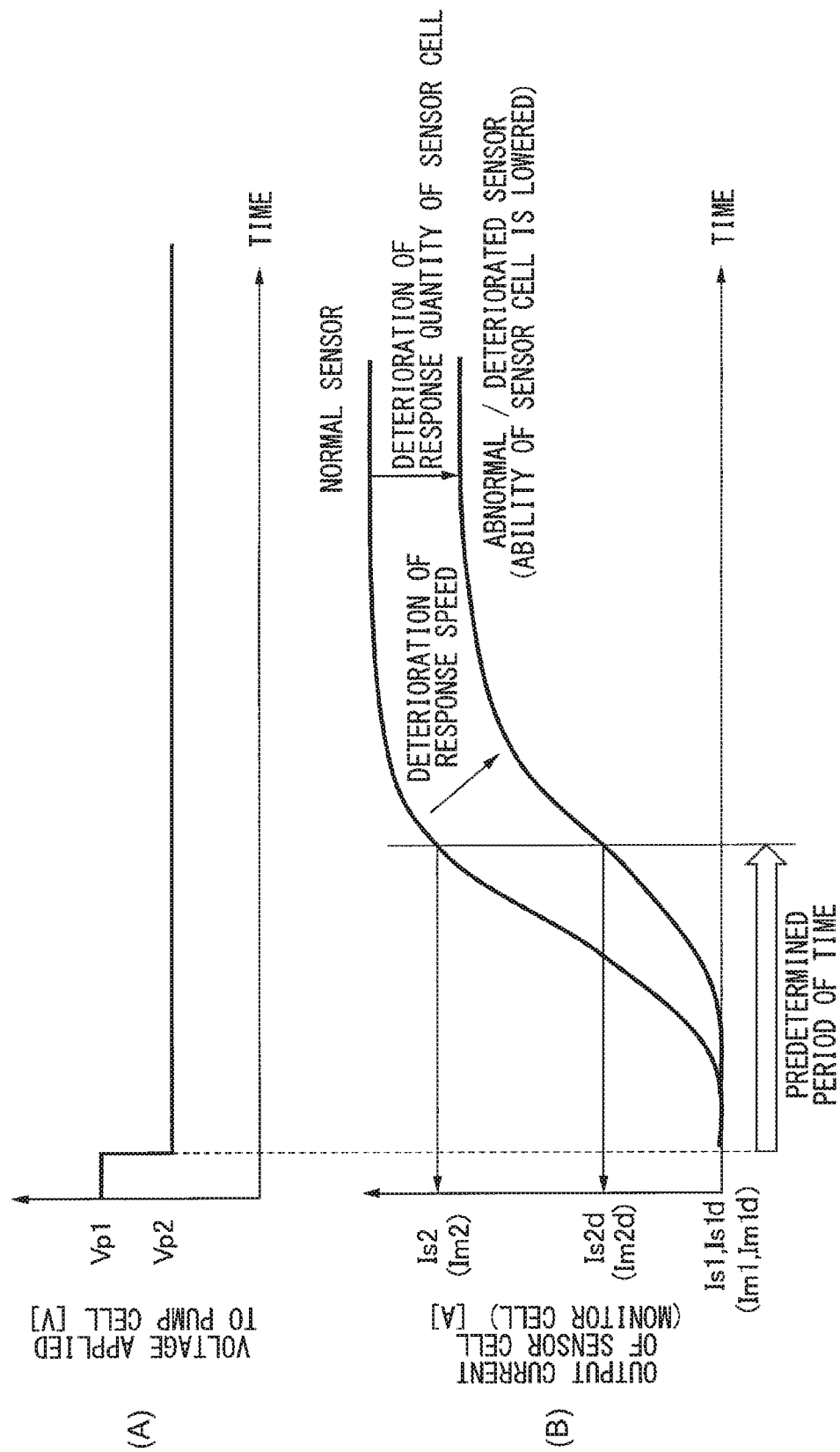
FIG. 8 is a graph illustrating the gas sensitivity determination processing that is illustrated in FIG. 4.

A relationship between the voltage applied to the pump cell 246 and the output current of the sensor cell 248 is illustrated in time series manner in FIG. 8. (A) of FIG. 8 shows the voltage applied to the pump cell 246 and (B) of FIG. 8 shows the output current of the sensor cell 248. FIG. 8 is an illustration relating to the sensor cell 248 and the illustration in FIG. 8 is common to both the sensor cell 248 and the monitor cell 249.

When the voltage applied to the pump cell 246 is lowered from Vp1 to Vp2, the output current of the pump cell 246 decreases and the amount of the oxygen supplied to the sensor cell 248 increases. As a result of the increase in the amount of the oxygen, the output current of the sensor cell 248 increases from Is1 to Is2. The rate of increase in the output current decreases when the sensor cell 248 deteriorates. Accordingly, it is found as a result of comparison between the output currents after the elapse of a predetermined period of time t that an output current Is2d during the deterioration decreases in comparison to the normal output current Is2.

The sensitivity determination unit 106 determines that the sensor cell 248 is deteriorated when the output current of the sensor cell 248 after the predetermined period of time t has elapsed since the lowering of the voltage applied to the pump cell 246 is lower than normal Is2 as in the case of Is2d illustrated in FIG. 8. When the gas sensitivity of the sensor cell 248 is grasped based on the tendency of the output current after the elapse of the predetermined period of time t as described above, the gas sensitivity can be grasped at a time determined in advance.

A determination based on a differential output current ΔIsd of the sensor cell 248 (=Is2d−Is1d) in the case of the lowering of the voltage applied to the pump cell 246 can be made in this case as well. When the differential output current ΔIsd is within a predetermined range, it can be determined that the sensitivity of the sensor cell 248 is normal and the deterioration of the sensor cell 248 is within the allowable range. During exhaust gas measurement, a voltage is applied to the pump cell 246, the sensor cell 248, and the monitor cell 249. Because of the voltage application, the current flows through the pump cell 246, the sensor cell 248, and the monitor cell 249 even in the event of no exhaust gas inflow and the current varies with temperature. Accordingly, it is preferable that the determination is made based on the differential output current ΔIsd for the effect attributable to the temperature difference to be ruled out.

In the first embodiment described above, the case of the fuel cut situation of the diesel engine 20 has been described as an example of the state where the exhaust gas has the stable state and the exhaust gas components are predictable. The state where the exhaust gas has the stable state and the exhaust gas components are predictable is not limited to the case of the fuel cut situation. As another example, IG-OFF can be detected and the gas sensitivity determination processing can be performed at that timing. IG-OFF results in no exhaust gas flow, and thus an exhaust gas environment is stabilized and the detection accuracy is improved. As another example, a soak timer can detect a time set in advance being reached after engine stop and the gas sensitivity determination processing can be performed at that timing. The exhaust gas environment is stabilized and the detection accuracy is improved in this case as well.

For the detection accuracy to be improved, it is preferable that the gas sensitivity determination processing described above is executed multiple times. The detection accuracy can be further improved by the gas sensitivity determination processing being executed multiple times and respective average values being used or extreme numerical values being ruled out.

For the detection accuracy to be improved, it is preferable that the voltage is applied to only one of the sensor cell 248 and the monitor cell 249 that is a detection object and the voltage application to the other one is stopped. Particularly preferable is to stop the voltage application to the monitor cell 249 and continue to apply the voltage to the sensor cell 248. This is because an improvement in NOx detection accuracy is a purpose and the gas sensitivity determination processing performed on the sensor cell 248, which is a cell to be directly detected, is preferable for the purpose.

Results of the gas sensitivity determination processing that is executed by the various methods described above can be used in various scenes. In one aspect of use, an abnormality and the degree of deterioration of the NOx sensor 24 are determined based on the divergence between a value measured when the NOx sensor 24 is a new product and values measured by the various methods described above (ratio between the output current of the sensor cell 248 and the output current of the monitor cell 249, output ratio Y/X, current absolute value, and sensor response speed). Use for correction of the output of the NOx sensor 24 can be performed based on a similar divergence comparison as well. Disconnection and electrode peeling can also be determined in a case where the divergence is excessive.

The first embodiment of the present disclosure has been described with reference to the specific examples. The present disclosure is not limited to the specific examples. In other words, appropriate changes in design being added to the specific examples by those skilled in the art are also included in the scope of the present disclosure insofar as the results of the addition still have the properties and features of the present disclosure. For example, the sensor current detection unit, the monitor current detection unit, the pump current detection unit, the voltage adjustment unit, the NOx concentration calculation unit, and the sensitivity determination unit may be configured as circuits separate from the ECU although the sensor current detection unit, the monitor current detection unit, the pump current detection unit, the voltage adjustment unit, the NOx concentration calculation unit, and the sensitivity determination unit according to the embodiment described above are configured to be disposed in the ECU 10.

Second Embodiment

An engine exhaust system ES2, in which the ECU 10 according to the first embodiment is divided into an ECU 10A and an SCU 40, will be described as a second embodiment with reference to FIGS. 9, 10, and 11.

Figure 9:
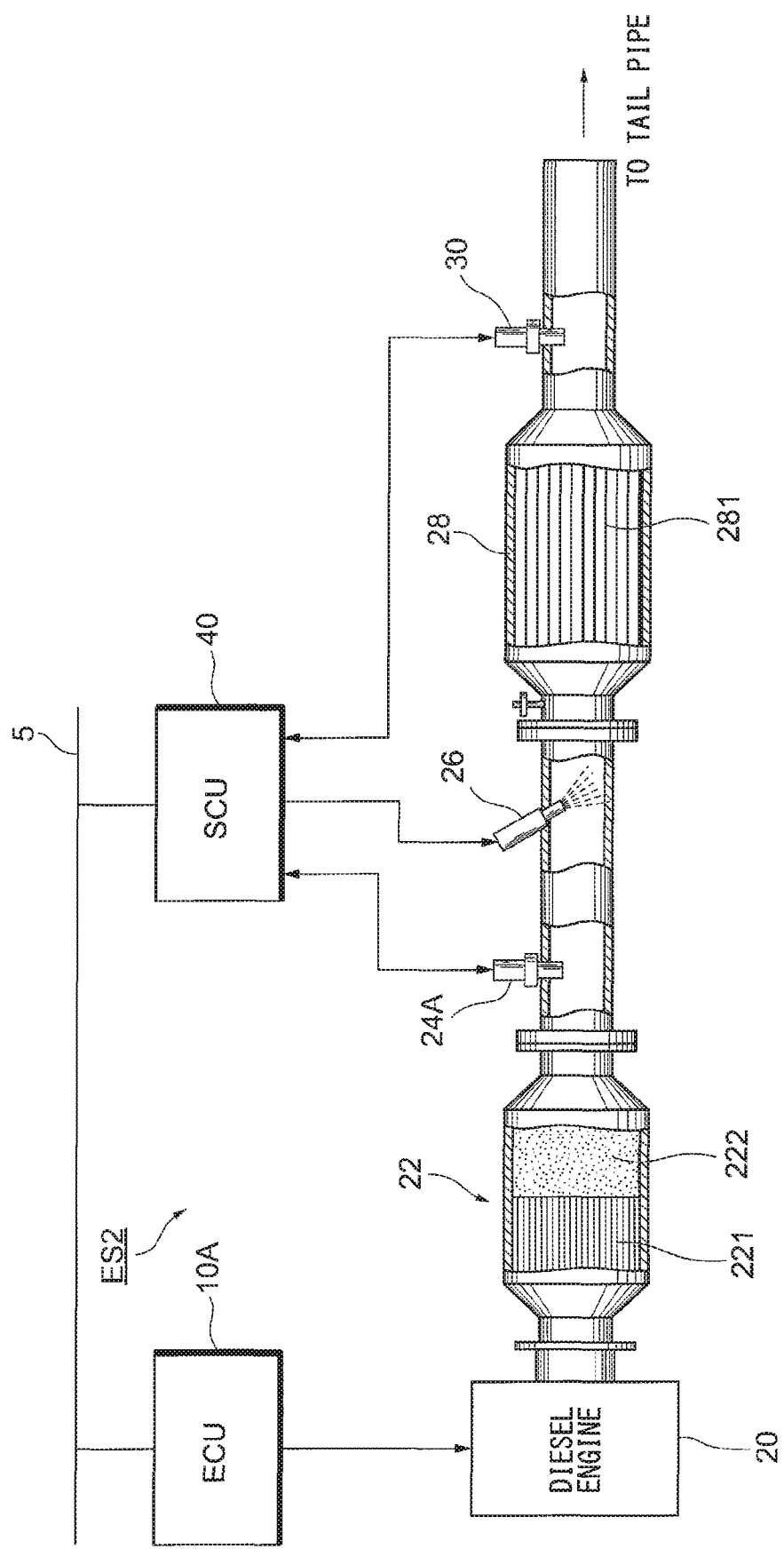
FIG. 9 is a diagram schematically illustrating an engine exhaust system in which an ECU and an SCU according to a second embodiment of the present disclosure are used.

As illustrated in FIG. 9, the engine control unit (ECU) 10A and the sensor control unit (SCU) 40 are disposed in the engine exhaust system ES2. The ECU 10A is a device that controls the diesel engine 20 and the engine exhaust system ES2 connected thereto. The ECU 10A functions to control a behavior of the diesel engine 20. The ECU 10A adjusts a fuel injection valve opening degree based on an accelerator opening degree and an engine rotation speed. The components other than the ECU 10A, the SCU 40, and a NOx sensor 24A are similar to those of the first embodiment, and thus description thereof will be omitted herein.

Currents outputted by the NOx sensor 24A and the NOx sensor 30 are detected by the SCU 40. The SCU 40 detects a gas amount, performs gas sensitivity determination processing, and transmits necessary data to the ECU 10A. The ECU 10A and the SCU 40 are connected to a controller area network (CAN) bus 5 and perform information communication via the CAN bus 5.

The SCU 40 includes a CPU, a RAM, a ROM, input/output ports, and a storage device. Because the NOx sensor 24A and the NOx sensor 30 have the same configuration, the following description will cover the configuration of the NOx sensor 24A as an example along with a configuration of the SCU 40.

Figure 10:
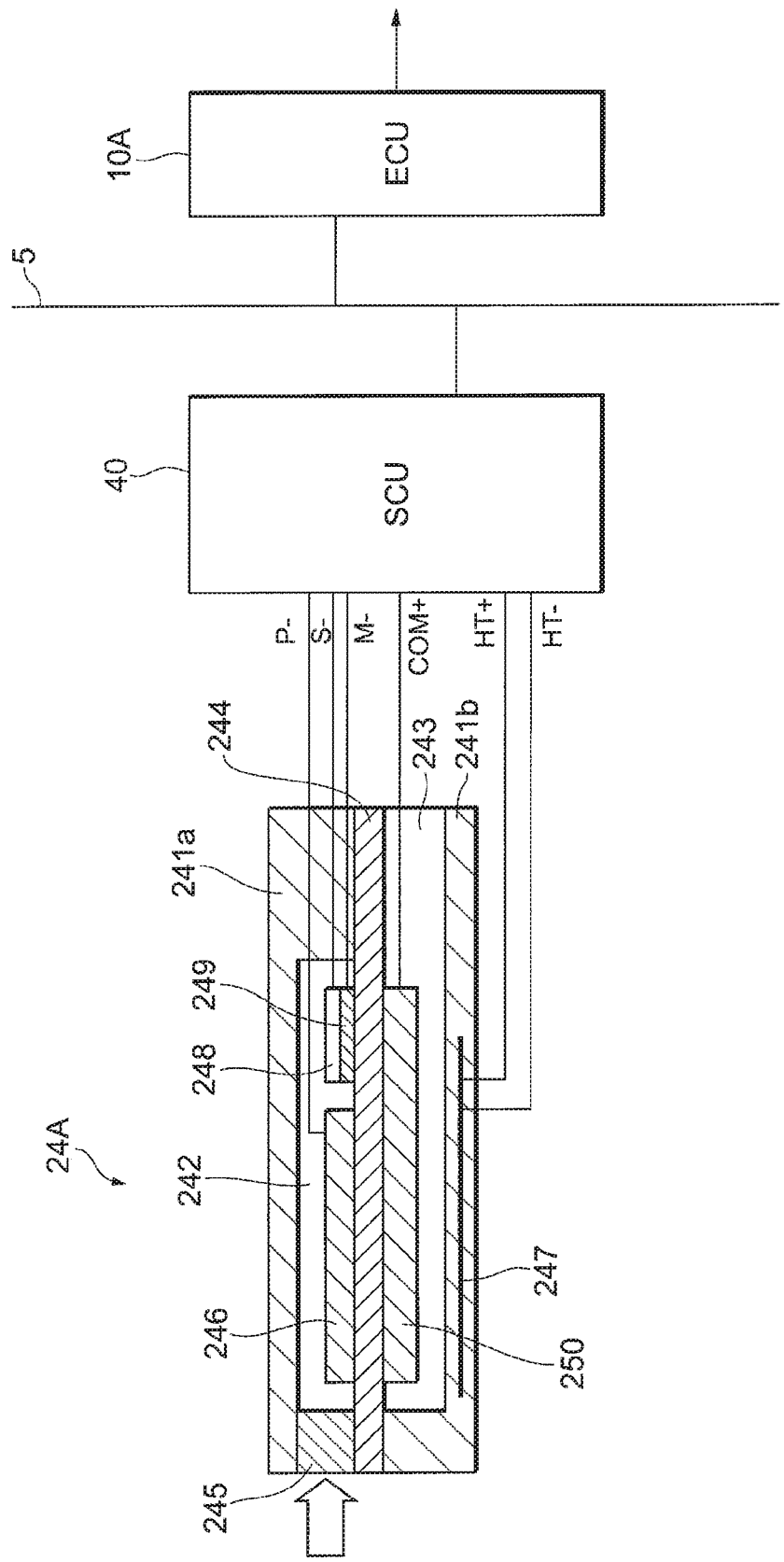
FIG. 10 is a diagram schematically illustrating a configuration of a NOx sensor that is illustrated in FIG. 9.
Figure 11:
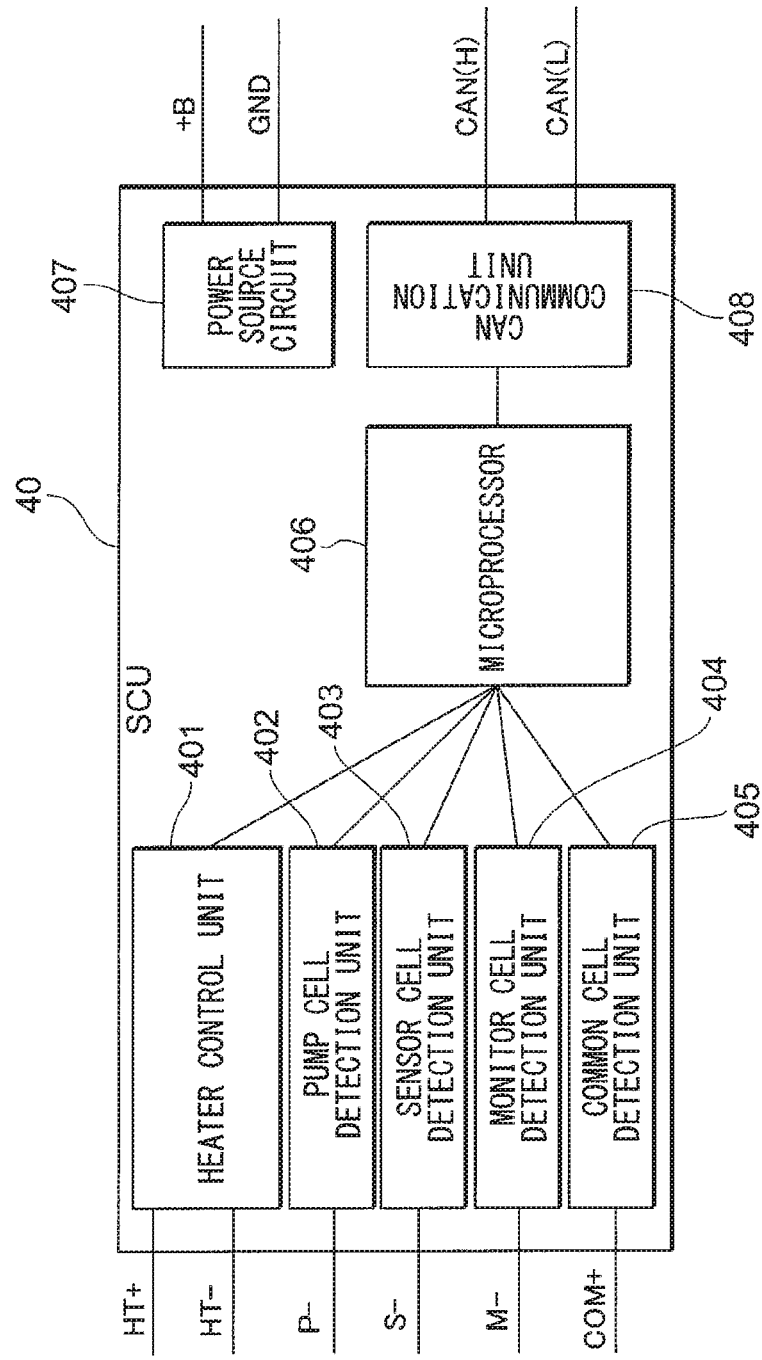
FIG. 11 is a diagram illustrating a control related configuration of the SCU that is illustrated in FIG. 10.

As illustrated in FIG. 10, the NOx sensor 24A is provided with the first main body portion 241*a*, the second main body portion 241*b*, the solid electrolyte body 244, the diffusion resistive element 245, the pump cell 246, the heater 247, the sensor cell 248, the monitor cell 249, and a common cell 250.

The solid electrolyte body 244 is a plate-shaped member and an oxygen ion-conducting solid electrolyte material such as zirconia oxide constitutes the solid electrolyte body 244. The first main body portion 241*a* and the second main body portion 241*b* are placed with the solid electrolyte body 244 placed therebetween. A recessed portion that is disposed to retreat from the solid electrolyte body 244 side is formed in the first main body portion 241*a* and the concave portion functions as the measurement chamber 242. One side surface of the measurement chamber 242 is open and the diffusion resistive element 245 is placed in the open side surface. The diffusion resistive element 245 is formed from a porous material or a material in which a pore is formed. A velocity of the exhaust gas that is drawn into the measurement chamber 242 is controlled by an action of the diffusion resistive element 245.

A recessed portion that is disposed to retreat from the solid electrolyte body 244 side is formed in the second main body portion 241*b* as well and the concave portion functions as the atmospheric chamber 243. One side surface of the atmospheric chamber 243 is open. Gas drawn into the atmospheric chamber 243 from the solid electrolyte body 244 side is released to the atmosphere.

The cathode side pump cell 246 is disposed on the diffusion resistive element 245 side and a surface of the solid electrolyte body 244 facing the measurement chamber 242 side. The anode side common cell 250 is disposed at a position corresponding to the pump cell 246 on a surface of the solid electrolyte body 244 facing the atmospheric chamber 243. The common cell 250 is disposed to cover up to a region corresponding to the sensor cell 248 and the monitor cell 249.

Once a voltage is applied between the pump cell 246 and the common cell 250, oxygen that is contained in the exhaust gas in the measurement chamber 242 comes into contact with the cathode side pump cell 246 and becomes an oxygen ion. The oxygen ion flows through the solid electrolyte body 244 toward the anode side common cell 250, becomes oxygen with its charge released in the common cell 250, and is discharged into the atmosphere from the atmospheric chamber 243.

The higher the voltage that is applied between the pump cell 246 and the common cell 250, the greater the amount of the oxygen that is discharged from the exhaust gas by the pump cell 246. The lower the voltage that is applied between the pump cell 246 and the common cell 250, the smaller the amount of the oxygen that is discharged from the exhaust gas by the pump cell 246. Accordingly, the amount of the residual oxygen that is contained in the exhaust gas which flows through the sensor cell 248 and the monitor cell 249 in a subsequent stage can be increased and decreased by the voltage applied between the pump cell 246 and the common cell 250 being increased and decreased.

The cathode side monitor cell 249 is disposed on the side opposite to the diffusion resistive element 245 across the pump cell 246 (downstream side the pump cell 246) and the surface of the solid electrolyte body 244 facing the measurement chamber 242 side. The anode side common cell 250 is disposed at a position corresponding to the monitor cell 249 on the surface of the solid electrolyte body 244 facing the atmospheric chamber 243.

The monitor cell 249 detects a concentration of the oxygen remaining in the exhaust gas from which the oxygen has been discharged by the pump cell 246. Once a voltage is applied between the monitor cell 249 and the common cell 250, the residual oxygen that is contained in the exhaust gas from which the oxygen has been discharged by the pump cell 246 comes into contact with the cathode side monitor cell 249 and becomes an oxygen on. The oxygen ion flows through the solid electrolyte body 244 toward the anode side common cell 250, becomes oxygen with its charge released in the common cell 250, and is discharged into the atmosphere from the atmospheric chamber 243, The charge at this time is detected as a current Im by a monitor cell detection unit 404 and the residual oxygen concentration in the exhaust gas can be calculated based on the current Im.

The cathode side sensor cell 248 is disposed on the side opposite to the diffusion resistive element 245 across the pump cell 246 and the surface of the solid electrolyte body 244 facing the measurement chamber 242 side. The anode side common cell is disposed at a position corresponding to the sensor cell 248 on the surface of the solid electrolyte body 244 facing the atmospheric chamber 243.

The sensor cell 248 has a platinum-rhodium alloy (Pt—Rh alloy) and has a high level of reducibility with respect to NOx. NOx brought into contact with the sensor cell 248 is subjected to reductive decomposition into $N_2$ and $O_2$. Once a voltage is applied between the sensor cell 248 and the common cell 250, $O_2$ resulting from the decomposition receives a charge from the cathode side sensor cell 248 and becomes an oxygen ion. The oxygen ion flows through the solid electrolyte body 244 toward the anode side common cell 250, becomes oxygen with its charge released in the common cell 250, and is discharged into the atmosphere from the atmospheric chamber 243. The charge at this time is detected as a current Is by a sensor cell detection unit 403 and the concentration of the NOx and the residual oxygen concentration in the exhaust gas can be calculated based on the current Is.

The SCU 40 is configured as a digital processor provided with a memory with an analog circuit constituting a part of the SCU 40 or the SCU 40 as a whole. In any of both cases, functional control blocks are configured in the SCU 40 for a function to output a control signal based on a received electrical signal to be achieved. FIG. 11 is a block diagram illustrating the functional control blocks of the SCU 40.

Functional components of the SCU 40 will be described below. The SCU 40 is provided with a heater control unit 401, a pump cell detection unit 402, the sensor cell detection unit 403, the monitor cell detection unit 404, a common cell detection unit 405, a microprocessor 406, a power source circuit 407, and a CAN communication unit 408.

The heater control unit 401 is a part that controls a voltage applied to the heater 247 and controls a heating value of the heater 247.

The pump cell detection unit 402 is a part that detects a current Ip and a voltage Vp outputted by the pump cell 246. The pump cell detection unit 402 outputs a signal indicating the detected current Ip and the detected voltage Vp to the microprocessor 406.

The sensor cell detection unit 403 is a part that detects the current Is outputted by the sensor cell 248. The sensor cell detection unit 403 outputs a signal indicating the detected current Is to the microprocessor 406.

The monitor cell detection unit 404 is a part that detects the current Im outputted by the monitor cell 249. The monitor cell detection unit 404 outputs a signal indicating the detected current Im to the microprocessor 406.

The common cell detection unit 405 is a part that detects a voltage Vcom outputted by the common cell 250. The common cell detection unit 405 outputs a signal indicating the detected voltage Vcom to the microprocessor 406.

The microprocessor 406 is a control unit in the SCU 40, The microprocessor 406 outputs a control signal for controlling a temperature of the heater 247 to the heater control unit 401. The microprocessor 406 is a part that calculates the NOx concentration in the exhaust gas based on the current Is detected by the sensor cell detection unit 403 and the current Im detected by the monitor cell detection unit 404. The microprocessor 406 calculates the NOx concentration in the exhaust gas excluding a current value attributable to the residual oxygen concentration in the exhaust gas detected by the sensor cell 248 by subtracting the output current Im outputted by the monitor cell 249 from the current Is outputted by the sensor cell 248. The microprocessor 406 outputs a signal indicating the calculated NOx concentration to the CAN communication unit 408.

The power source circuit 407 is a power source circuit in the SCU 40. The CAN communication unit 408 transmits the signal outputted by the microprocessor 406 to the CAN bus 5 and outputs a signal received from the CAN bus 5 to the microprocessor 406.

In the second embodiment, a functional part equivalent to the sensitivity determination unit 106 according to the first embodiment is configured in the microprocessor 406. Accordingly, the gas sensitivity determination processing can be executed as in the first embodiment.

Third Embodiment

A NOx sensor in which a pump cell and a sensor cell are disposed in different chambers separated from each other can be used as well as a NOx sensor in which the pump cell 246 and the sensor cell 248 are disposed in a single chamber as in the case of the NOx sensor 24 according to the first embodiment and as in the case of the NOx sensor 24A according to the second embodiment.

Figure 12:
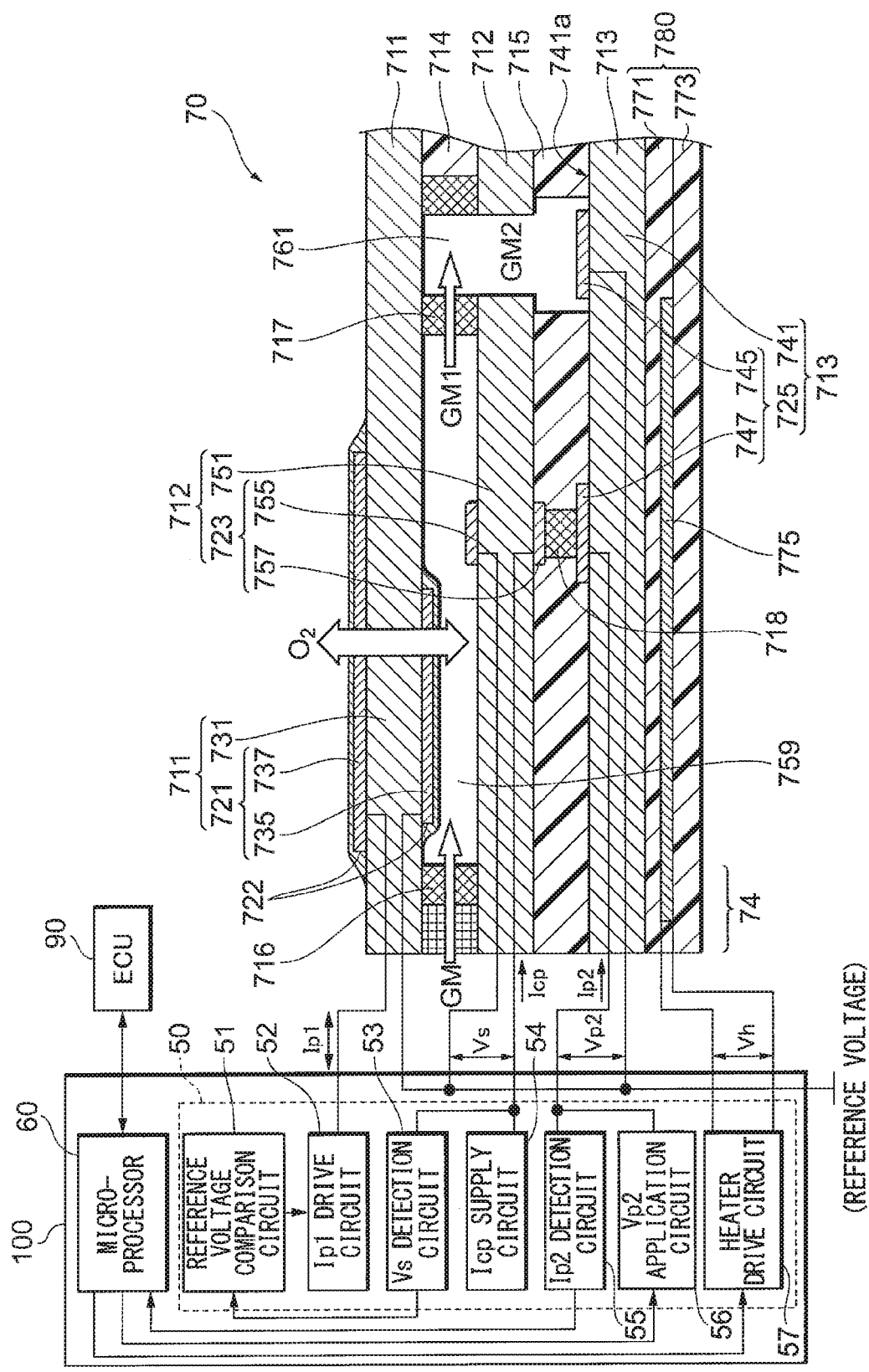
FIG. 12 is a configuration diagram schematically illustrating a third embodiment of the present disclosure.

FIG. 12 is a diagram illustrating schematic configurations of a gas sensor control device 100 and a NOx sensor 70 according to a third embodiment.

The gas sensor control device 100 and the NOx sensor 70 are mounted in a vehicle that is provided with an internal combustion engine. NOx concentration in exhaust gas of the engine is detected by the NOx sensor 70 being controlled by the gas sensor control device 100.

In the following description, a left side in FIG. 12 is a tip side of the NOx sensor 70 and a right side in FIG. 12 is a rear end side of the NOx sensor 70.

A first pump cell 711, an insulating layer 714, an oxygen concentration detection cell 712, an insulating layer 715, and a second pump cell 713 are stacked to constitute the NOx sensor 70. The insulating layers 714 and 715 have alumina as their main raw materials. A heater unit 780 is stacked on the second pump cell 713 side of the NOx sensor 70.

The first pump cell 711 is provided with a first solid electrolyte layer 731 and a pair of first porous electrodes 721. The first solid electrolyte layer 731 has a solid electrolyte body that has oxygen ion conductivity and has zirconia as its main component. The pair of first porous electrodes 721 is placed for the first solid electrolyte layer 731 to be inserted therebetween. The pair of first porous electrodes 721 has platinum as their main raw material. The first porous electrode 721 has a first electrode 735 for a first pump and a second electrode 737 for the first pump. Each surface of the first electrode 735 for the first pump and the second electrode 737 for the first pump is covered by a protective layer 722 that has a porous body.

The oxygen concentration detection cell 712 is provided with a third solid electrolyte layer 751 and a pair of porous electrodes 723 for detection. The third solid electrolyte layer 751 has a solid electrolyte body that has zirconia as its main component. The pair of porous electrodes 723 for detection is placed for the third solid electrolyte layer 751 to be inserted therebetween. The pair of porous electrodes 723 for detection has platinum as their main raw material. The porous electrode 723 for detection has an electrode 755 for detection and an electrode 757 for reference.

The second pump cell 713 is provided with a second solid electrolyte layer 741 and a pair of second porous electrodes 725. The second solid electrolyte layer 741 has a solid electrolyte body that has zirconia as its main component. The pair of second porous electrodes 725 is placed on a surface 741a of the second solid electrolyte layer 741 on a side facing the insulating layer 715. The pair of second porous electrodes 725 has platinum as their main raw material. The second porous electrode 725 has a first electrode 745 for a second pump and a second electrode 747 for the second pump.

A first measurement chamber 759 is formed in the NOx sensor 70. Gas GM to be measured is introduced from the outside into the first measurement chamber 759 via a first diffusion resistive element 716. The first diffusion resistive element 716 is placed between the first pump cell 711 and the oxygen concentration detection cell 712.

A porous body constitutes the first diffusion resistive element 716. The first diffusion resistive element 716 is placed in an introduction path 74 for the gas GM to be measured that reaches the first measurement chamber 759 from a tip side (left side in the drawing) opening portion of the NOx sensor 70. The first diffusion resistive element 716 limits the amount of introduction (amount of passage) per unit time of the gas GM to be measured into the first measurement chamber 759.

A second diffusion resistive element 717 is placed on a rear end side of the first measurement chamber 759 (right side in the drawing) in the NOx sensor 70. A second measurement chamber 761 is formed further on the rear end side than the second diffusion resistive element 717. The second diffusion resistive element 717 has a porous body. In-first chamber gas GM1 in the first measurement chamber 759 is introduced into the second measurement chamber 761 via the second diffusion resistive element 717. The second measurement chamber 761 is formed to penetrate the insulating layers 714 and 715 and the oxygen concentration detection cell 712 in a stacking direction. The first electrode 745 for the second pump of the second pump cell 713 faces the second measurement chamber 761.

A reference oxygen chamber 718 is formed between the third solid electrolyte layer 751 of the oxygen concentration detection cell 712 and the second solid electrolyte layer 741 of the second pump cell 713 in the NOx sensor 70. The reference oxygen chamber 718 is surrounded by the third solid electrolyte layer 751, the second solid electrolyte layer 741 and the insulating layer 715. The electrode 757 for reference of the oxygen concentration detection cell 712 and the second electrode 747 for the second pump of the second pump cell 713 are placed to face the reference oxygen chamber 718.

Insulating layers 771 and 773 are stacked to constitute the heater unit 780. The insulating layers 771 and 773 are sheet-shaped parts that have insulating ceramic such as alumina. The heater unit 780 is provided with a heater heat generation pattern 775, which has platinum as its main component, between the insulating layers 771 and 773. The heater unit 780 generates heat by a current flowing through the heater heat generation pattern 775.

The gas sensor control device 100 will be described below. A microprocessor 60 and an electric circuit portion 50 are main components of the gas sensor control device 100. The electric circuit portion 50 is electrically connected to the NOx sensor 70.

The microprocessor 60 is connected to an ECU 90. Accordingly, the microprocessor 60 in the gas sensor control device 100 controls driving of the NOx sensor 70 and detects the NOx concentration in the exhaust gas in accordance with an instruction from the ECU 90.

The electric circuit portion 50 is provided with a reference voltage comparison circuit 51, an Ip1 drive circuit 52, a Vs detection circuit 53, an Icp supply circuit 54, an Ip2 detection circuit 55, a Vp2 application circuit 56, and a heater drive circuit 57.

The Icp supply circuit 54 supplies a small self-generated current Iop between the electrode 755 for detection and the electrode 757 for reference of the oxygen concentration detection cell 712. As a result, oxygen can be pumped out of the first measurement chamber 759 and into the reference oxygen chamber 718 and the reference oxygen chamber 718 can be set to a predetermined oxygen concentration atmosphere.

The Vs detection circuit 53 detects a concentration detection voltage Vs between the electrode 755 for detection and the electrode 757 for reference of the oxygen concentration detection cell 712 and outputs the detected concentration detection voltage Vs to the reference voltage comparison circuit 51.

The reference voltage comparison circuit 51 compares the concentration detection voltage Vs detected by the Vs detection circuit 53 to a reference voltage set in advance and outputs the comparison result toward the Ip1 drive circuit 52.

The Ip1 drive circuit 52 supplies a first pump current Ip1 between the first electrode 735 for the first pump and the second electrode 737 for the first pump of the first pump cell 711. The Ip1 drive circuit 52 controls a magnitude and a direction of the first pump current Ip1, based on the comparison result by the reference voltage comparison circuit 51, such that the concentration detection voltage Vs becomes equal to the reference voltage. In the first pump cell 711, oxygen is pumped out of the NOx sensor 70 from an inner portion of the first measurement chamber 759 or oxygen is pumped into the first measurement chamber 759 from the outside of the NOx sensor 70 as a result.

As described above, the first pump current Ip1 flowing through the first pump cell 711 is controlled such that the concentration detection voltage Vs between the electrode 755 for detection and the electrode 757 for reference of the oxygen concentration detection cell 712 is maintained at the reference voltage set in advance. As a result, oxygen concentration of the in-first chamber gas GM1 in the first measurement chamber 759 can be controlled at a predetermined concentration (first concentration).

The in-first chamber gas GM1 that is controlled at the first concentration is introduced into the second measurement chamber 761 via the porous second diffusion resistive element 717.

The Vp2 application circuit 56 applies a second pump voltage Vp2 between the first electrode 745 for the second pump and the second electrode 747 for the second pump of the second pump cell 713. The second pump voltage Vp2 is a detection voltage Vp2a determined in advance during detection of a specific gas (NOx) concentration.

In the second measurement chamber 761, NOx in the second chamber gas GM2 in the second measurement chamber 761 is dissociated by catalysis of the first electrode 745 for the second pump of the second porous electrode 725 constituting the second pump cell 713. An oxygen ion resulting from the dissociation moves through the second solid electrolyte layer 741 and a second pump current Ip2 corresponding to the specific gas (NOx) concentration flows between the first electrode 745 for the second pump and the second electrode 747 for the second pump.

The second pump cell 713 dissociates a specific gas component (NOx) that is present in the second chamber gas GM2 in the second measurement chamber 761 and pumps oxygen from the second measurement chamber 761 to the reference oxygen chamber 718.

The Ip2 detection circuit 55 detects a magnitude of the second pump current Ip2 flowing between the first electrode 745 for the second pump and the second electrode 747 for the second pump.

The heater drive circuit 57 is controlled by the microprocessor 60, controls energization of the heater unit 780 toward the heater heat generation pattern 775, and causes the heater unit 780 to generate heat. As a result, the first solid electrolyte layer 731 of the first pump cell 711, the oxygen concentration detection cell 712, the third solid electrolyte layer 751, and the second solid electrolyte layer 741 of the second pump cell 713 are heated up to an activation temperature (such as 750° C.).

In the third embodiment, a functional part equivalent to the sensitivity determination unit 106 according to the first embodiment is configured in the microprocessor 60. Accordingly, the gas sensitivity determination processing can be executed as in the first embodiment.

According to the embodiments described above, the voltage adjustment unit 104 (and the functionally equivalent to the microprocessors 406 and 60 and the electric circuit portion 50) changes the pump cell voltage from the target voltage into the detection voltage such that the concentration of the residual oxygen supplied to the sensor cell 248 and the monitor cell 249 is increased and the sensitivity determination unit 106 (and the functionally equivalent to the microprocessors 406 and 60 and the electric circuit portion 50) determines the gas sensitivity based on the detection current detected by at least one of the sensor current detection unit 101 (or the functionally equivalent to the sensor cell detection unit 403 or the electric circuit portion 50) or the monitor current detection unit (or the functionally equivalent to the monitor cell detection unit 404 or the electric circuit portion 50) in accordance with the increased residual oxygen concentration.

According to the embodiments described above, the pump cell voltage is lowered from the target voltage and becomes the detection voltage, and thus the oxygen corresponding to the detection voltage flows from the pump cell 246 (and first pump cell 711 and second pump cell 713) side to the monitor cell 249 and sensor cell 248 (and oxygen concentration detection cell 712) sides. The residual oxygen concentration in the case of voltage application to the pump cell 246 at the detection voltage exceeds the residual oxygen concentration in the case of voltage application to the pump cell 246 at the target voltage. Because the currents outputted by the monitor cell 249 and the sensor cell 248 are currents corresponding to the residual oxygen concentration, the detection current of the deteriorated cell is lowered as a result of the deterioration when one of the monitor cell 249 and the sensor cell 248 deteriorates and its gas sensitivity is reduced, and thus the deterioration of that cell can be grasped. In this manner, the gas sensitivity can be determined without the concentration of the gas in the exhaust gas to be measured having to be fluctuated to a significant extent.

According to the embodiments described above, the voltage adjustment unit 104 sets the detection voltage while monitoring the detection current such that the detection current that is monitored becomes a measurable current. Since the detection voltage is set during the monitoring of the detection current that is an output current, the detection voltage can be set even if the detection current is weak.

According to the embodiments described above, the voltage adjustment unit 104 is capable of monitoring the detection current while lowering the pump cell voltage at a predetermined rate from the target voltage. The detection current fluctuates as a result of the decline in the pump cell voltage at the predetermined rate, and thus the fluctuation of the detection current can be grasped with ease.

According to the embodiments described above, the voltage adjustment unit 104 is capable of setting the detection voltage such that the detection current is in proximity to the maximum value of the measurable current. By the setting being performed such that the detection current is in proximity to the maximum value of the measurable current, the detection current can be acquired as a high current value and the fluctuation of the detection current can be grasped with ease.

According to the embodiments described above, the detection voltage includes the first detection voltage and the second detection voltage that is lower than the first detection voltage, the voltage adjustment unit 104 is capable of setting the pump cell voltage to each of the first detection voltage and the second detection voltage, and the sensitivity determination unit 106 is capable of determining the gas sensitivity based on each of the detection current corresponding to the first detection voltage and the detection current corresponding to the second detection voltage. Since the first detection voltage and the second detection voltage that are lower than the target voltage are used, a detection current in a region with a higher level of stability can be acquired.

According to the embodiments described above, the engine control unit 107 that is equivalent to a fuel control unit is capable of controlling the fuel to be in a cut-off state where no fuel is supplied to the diesel engine 20 and the sensitivity determination unit 106 is capable of determining the gas sensitivity of at least one of the sensor cell 248 or the monitor cell 249 under the cut-off state. By the diesel engine 20 being put into the cut-off state, the detection current can be acquired in the state where the exhaust gas has the stable state and the exhaust gas components are predictable.

The detection of the output current of the monitor cell 249 according to the embodiments described above is not essential. Therefore, according to the embodiments described above, the voltage adjustment unit 104 is capable of changing the pump cell voltage such that the concentration of the residual oxygen supplied to the sensor cell 248 is increased and the sensitivity determination unit 106 is capable of determining the gas sensitivity based on the detection current detected by the sensor current detection unit 101 in accordance with the increased residual oxygen concentration.

According to the embodiments described above, the pump cell voltage is lowered from the target voltage and becomes the detection voltage, and thus the oxygen corresponding to the detection voltage flows from the pump cell 246 side to the sensor cell 248 side. The residual oxygen concentration in the case of voltage application to the pump cell 246 at the detection voltage exceeds the residual oxygen concentration in the case of voltage application to the pump cell 246 at the target voltage. Because the current outputted by the sensor cell 248 is a current corresponding to the residual oxygen concentration, the detection current of the deteriorated cell is lowered as a result of the deterioration when one of the sensor cells 248 deteriorates and its gas sensitivity is reduced, and thus the deterioration of that cell can be grasped. In this manner, the gas sensitivity can be determined without the concentration of the gas in the exhaust gas to be measured having to be fluctuated to a significant extent.

According to the embodiments described above, the voltage adjustment unit 104 is capable of changing the voltage applied to the pump cell 246 into the even lower detection voltage from a discharge voltage (target voltage) at which the oxygen is discharged out of the measurement chamber 242 and the sensitivity determination unit 106 is capable of determining the gas sensitivity based on a change in the current detected by the sensor current detection unit 101 that is generated as a result of the change in the voltage applied to the pump cell 246. Oxygen supply to the sensor cell 248 side can be performed as a result of the change into the even lower detection voltage from the discharge voltage (target voltage) at which the oxygen is discharged out of the measurement chamber 242, and thus the current detected by the sensor current detection unit 101 changes and the gas sensitivity can be determined.

According to the embodiments described above, the pump current detection unit 103 that detects the current flowing through the pump cell 246 is provided and the detection voltage can be a voltage at which the current detected by the pump current detection unit 103 has a current value lower than a current value at a time when the discharge voltage is applied to the pump cell. A more stable detection current can be acquired by the detection voltage being the voltage at which the current detected by the pump current detection unit 103 has the current value lower than the current value at the time when the discharge voltage is applied to the pump cell as described above.

According to the embodiments described above, the voltage adjustment unit 104 is capable of changing the voltage applied to the pump cell 246 into the even lower detection voltage from the discharge voltage at which the oxygen is discharged out of the measurement chamber 242 and the sensitivity determination unit 106 is capable of determining the gas sensitivity based on a change in the current detected by the sensor current detection unit 101 after a predetermined period of time has elapsed since the change in the voltage applied to the pump cell 246. When the gas sensitivity of the sensor cell 248 is grasped based on the tendency of the output current after the elapse of the predetermined period of time as described above, the gas sensitivity can be grasped at a time determined in advance.

According to the embodiments described above, the residual oxygen concentration detection by the monitor cell 249 can be stopped before the gas sensitivity is determined by the sensitivity determination unit 106 in a case where the monitor cell 249 that detects the residual oxygen concentration in the exhaust gas from which the oxygen is discharged is provided. The gas sensitivity detection accuracy of the sensor cell 248 can be enhanced when the detection by the monitor cell 249 is stopped as described above.

In the first embodiment and the second embodiment described above, the pump cell 246 and the sensor cell 248 are disposed in the same and unpartitioned space (measurement chamber 242). No partition is required and a compact configuration can be achieved by the pump cell 246 and the sensor cell 248 being disposed in the same space as described above.

The respective elements of the specific examples described above and their placement, materials, conditions, shapes, sizes, and so on are not limited to the content of the exemplification and can be appropriately modified. In addition, the respective elements of the embodiments described above can be combined insofar as the combination is technically available, and such combinations are included in the scope of the present disclosure insofar as the combinations have the properties and features of the present disclosure.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

The invention claimed is:

1. A gas concentration detection device comprising:
 a pump cell configured to discharge oxygen out of a measurement chamber from an exhaust gas of an internal combustion engine introduced into the measurement chamber;
 a sensor cell configured to detect a residual oxygen concentration in the exhaust gas from which the oxygen is discharged and a specific gas concentration in the exhaust gas;
 a monitor cell configured to detect the residual oxygen concentration in the exhaust gas from which the oxygen is discharged; and
 a processor coupled to the pump cell and the sensor cell, wherein
 the pump cell and the sensor cell are disposed in a common space that is unpartitioned, and the processor is programmed to:
  determine whether the exhaust gas is in a stable state, the stable state being defined as a state in which an ignition of the internal combustion engine is detected to be OFF or a state in which the internal combustion engine is in a fuel cut situation, and
  upon determining that the exhaust gas is in the stable state:
    reduce a pump cell voltage applied to the pump cell,
    determine a first current change which is a change in an output current of the pump cell during the reducing of the pump cell voltage,
    determine a second current change which is a change in an output current of the sensor cell during the reducing of the pump cell voltage, and
    determine whether an abnormality exists in the sensor cell based on whether a ratio between the first current change and the second current change is outside of a predetermined range.

2. The gas concentration detection device according to claim 1, wherein
the processor is further programmed to reduce the pump cell voltage until the output current of the sensor cell becomes a measurable current.

3. The gas concentration detection device according to claim 2, wherein
the processor is further programmed to reduce the pump cell voltage until the output current of the sensor cell is in proximity to a maximum measurable current value.

4. The gas concentration detection device according to claim 1, wherein
the processor is further programmed to, after determining whether the abnormality exists in the sensor cell, further reduce the pump cell voltage and then perform a second determination of whether the abnormality exists in the sensor cell based on changes in the output currents of the pump cell and the sensor cell during the further reduction of the pump cell voltage.

5. The gas concentration detection device according to claim 1, wherein
the specific gas is different from oxygen.

6. The gas concentration detection device according to claim 1, wherein
the specific gas is NOx.

7. The gas concentration detection device according to claim 1, wherein the processor is further programmed to:
  change the voltage applied to the pump cell into an even lower detection voltage from a discharge voltage at which the oxygen is discharged out of the measurement chamber, and
  determine a gas sensitivity based on the change in the output current of the sensor cell generated as a result of the change in the voltage applied to the pump cell.

8. The gas concentration detection device according to claim 7, wherein the processor is further configured to execute the determination of the gas sensitivity multiple times.

9. The gas concentration detection device according to claim 7, wherein the processor is further configured to perform the determination of the gas sensitivity when voltage application to the monitor cell is stopped and voltage application to the sensor cell is continued.

10. A gas concentration detection device comprising:
a pump cell configured to discharge oxygen out of a measurement chamber from an exhaust gas of an internal combustion engine introduced into the measurement chamber;
a sensor cell configured to detect a concentration of a residual oxygen in the exhaust gas from which the oxygen is discharged and a specific gas concentration in the exhaust gas; and
a processor coupled to the pump cell and the sensor cell, wherein
the pump cell and the sensor cell are disposed in a common space that is unpartitioned, and
the processor is programmed to:
  determine whether the exhaust gas is in a stable state, the stable state being defined as a state in which an ignition of the internal combustion engine is detected to be OFF or a state in which the internal combustion engine is in a fuel cut situation, and
  upon determining that the exhaust gas is in the stable state:
    reduce a pump cell voltage applied to the pump cell,
    determine a first current change which is a change in an output current of the pump cell during the reducing of the pump cell voltage,
    determine a second current change which is a change in an output current of the sensor cell during the reducing of the pump cell voltage, and
    determine whether an abnormality exists in the sensor cell based on whether a ratio between the first current change and the second current change is outside of a predetermined range.

11. The gas concentration detection device according to claim 10, wherein the processor is further programmed to:
  change the voltage applied to the pump cell into an even lower detection voltage from a discharge voltage at which the oxygen is discharged out of the measurement chamber, and
  determine a gas sensitivity based on the change in the output current of the sensor cell generated as a result of the change in the voltage applied to the pump cell.

12. The gas concentration detection device according to claim 11, wherein the processor is further programmed to:
  detect the current flowing through the pump cell, wherein the detection voltage is a voltage at which the output current of the pump cell has a current value lower than a current value at a time when the discharge voltage is applied to the pump cell.

13. The gas concentration detection device according to claim 11, further comprising:
a monitor cell configured to detect the concentration of the residual oxygen in the exhaust gas from which the oxygen is discharged, wherein
the monitor cell is configured to stop the residual oxygen concentration detection before the gas sensitivity is determined.

14. The gas concentration detection device according to claim 13, wherein the processor is further configured to perform the determination of the gas sensitivity when voltage application to the monitor cell is stopped and voltage application to the sensor cell is continued.

15. The gas concentration detection device according to claim 11, wherein the processor is further configured to execute the determination of the gas sensitivity multiple times.

16. The gas concentration detection device according to claim 10, wherein the processor is further programmed to:
  change the voltage applied to the pump cell into an even lower detection voltage from a discharge voltage at which the oxygen is discharged out of the measurement chamber, and determine a gas sensitivity based on the change in the output current of the sensor cell after a predetermined period of time has elapsed since the change in the voltage applied to the pump cell.

17. The gas concentration detection device according to claim 10, wherein
the specific gas is different from oxygen.

18. The gas concentration detection device according to claim 10, wherein
the specific gas is NOx.

* * * * *